United States Patent
Amit et al.

(10) Patent No.: US 10,303,835 B2
(45) Date of Patent: May 28, 2019

(54) METHOD AND APPARATUS FOR DIRECT SELF ASSEMBLY IN TARGET DESIGN AND PRODUCTION

(71) Applicant: KLA-TENCOR CORPORATION, Milpitas, CA (US)

(72) Inventors: Eran Amit, Haifa (IL); Raviv Yohanan, Qiryat Motzkin (IL); Tal Itzkovich, Kfar Yriya (IL); Nuriel Amir, St. Yokne'am (IL); Roie Volkovich, Hadera (IL); Dongsub Choi, Yongin (KR)

(73) Assignee: KLA-Tencor Corporation, Milpitas, CA (US)

( * ) Notice: Subject to any disclaimer, the term of this patent is extended or adjusted under 35 U.S.C. 154(b) by 714 days.

(21) Appl. No.: 14/710,201

(22) Filed: May 12, 2015

(65) Prior Publication Data
US 2015/0242558 A1  Aug. 27, 2015

Related U.S. Application Data

(63) Continuation of application No. PCT/US2014/033621, filed on Apr. 10, 2014.
(Continued)

(51) Int. Cl.
*B32B 3/10* (2006.01)
*G06F 17/50* (2006.01)
(Continued)

(52) U.S. Cl.
CPC ......... *G06F 17/5072* (2013.01); *G01N 21/93* (2013.01); *G01N 21/956* (2013.01); *G03F 7/0002* (2013.01); *H01L 21/3105* (2013.01); *H01L 21/31058* (2013.01); *H01L 21/31138* (2013.01); *Y10T 428/24802* (2015.01)

(58) Field of Classification Search
None
See application file for complete search history.

(56) References Cited

U.S. PATENT DOCUMENTS 7,767,265 B2  8/2010  Yoshida et al.
8,243,273 B2  8/2012  Levinski et al.
(Continued)

FOREIGN PATENT DOCUMENTS

JP  2007128087 A  5/2007
JP  2007313568 A  12/2007

*Primary Examiner* — Christopher M Polley
(74) *Attorney, Agent, or Firm* — Suiter Swantz pc llo

(57) ABSTRACT

Target designs methods and targets are provided, in which at least some of the differentiation between target elements and their background is carried out by segmenting either of them. Directed self-assembly (DSA) processes are used to generate fine segmentation, and various characteristics of the polymer lines and their guiding lines are used to differentiate target elements from their background. Target designs and design principles are disclosed in relation to the DSA process, as well as optimization of the DSA process to yield high metrology measurement accuracy in face of production inaccuracies. Furthermore, designs and methods are provided for enhancing and using ordered regions of a DSA-produced polymer surface as target elements and as hard masks for production processes. The targets and methods may be configured to enable metrology measurements using polarized light to distinguish target elements or DSA features.

26 Claims, 34 Drawing Sheets

Related U.S. Application Data

(60) Provisional application No. 61/866,546, filed on Aug. 16, 2013, provisional application No. 61/829,128, filed on May 30, 2013, provisional application No. 61/810,995, filed on Apr. 11, 2013, provisional application No. 61/810,637, filed on Apr. 10, 2013.

(51) Int. Cl.
| | | |
|---|---|---|
| *G01N 21/93* | (2006.01) | |
| *G01N 21/956* | (2006.01) | |
| *H01L 21/3105* | (2006.01) | |
| *H01L 21/311* | (2006.01) | |
| *G03F 7/00* | (2006.01) | |

(56) References Cited

U.S. PATENT DOCUMENTS

| | | |
|---|---|---|
| 8,687,274 B2 | 4/2014 | Asakawa et al. |
| 2004/0175628 A1 | 9/2004 | Nealey et al. |
| 2011/0147984 A1 | 6/2011 | Cheng et al. |
| 2012/0033215 A1 | 2/2012 | Kandel et al. |
| 2013/0059438 A1 | 3/2013 | Zhou et al. |
| 2013/0293890 A1 | 11/2013 | Amir et al. |
| 2014/0065736 A1 | 3/2014 | Amir et al. |

*200*

- 205 — PRODUCING A POLYMER SURFACE BY A DIRECTED SELF-ASSEMBLY (DSA) PROCESS
- 210 — SELECTING ROD-LIKE MOLECULES TO BIND TO LINEARLY ORDERED POLYMER MOLECULES STRONGER THAN TO UNORDERED POLYMER MOLECULES
- 212 — SELECTING THE ROD-LIKE MOLECULES FROM CELLULOSE, NANOTUBES AND RIGID-ROD POLYMERS
- 213 — SELECTING THE ROD-LIKE MOLECULES TO BE CELLULOSE MOLECULES HAVING A CRYSTALLINE FORM WHICH DEPENDS UPON A LEVEL OF ORDER IN THE BOUND REGION
- 215 — CREATING TOPOGRAPHICAL DIFFERENCES BETWEEN THE ORDERED AND THE UNORDERED REGIONS
- 218 — AT LEAST PARTLY ETCHING AWAY THE UNORDERED REGIONS
- 220 — BINDING ROD-LIKE MOLECULES ONTO A POLYMER SURFACE WHICH COMPRISES ORDERED REGIONS AND UNORDERED REGIONS
- 222 — CONFIGURING THE ROD-LIKE MOLECULES TO COMPRISE BRIDGING MOLECULE(S)

Figure 25

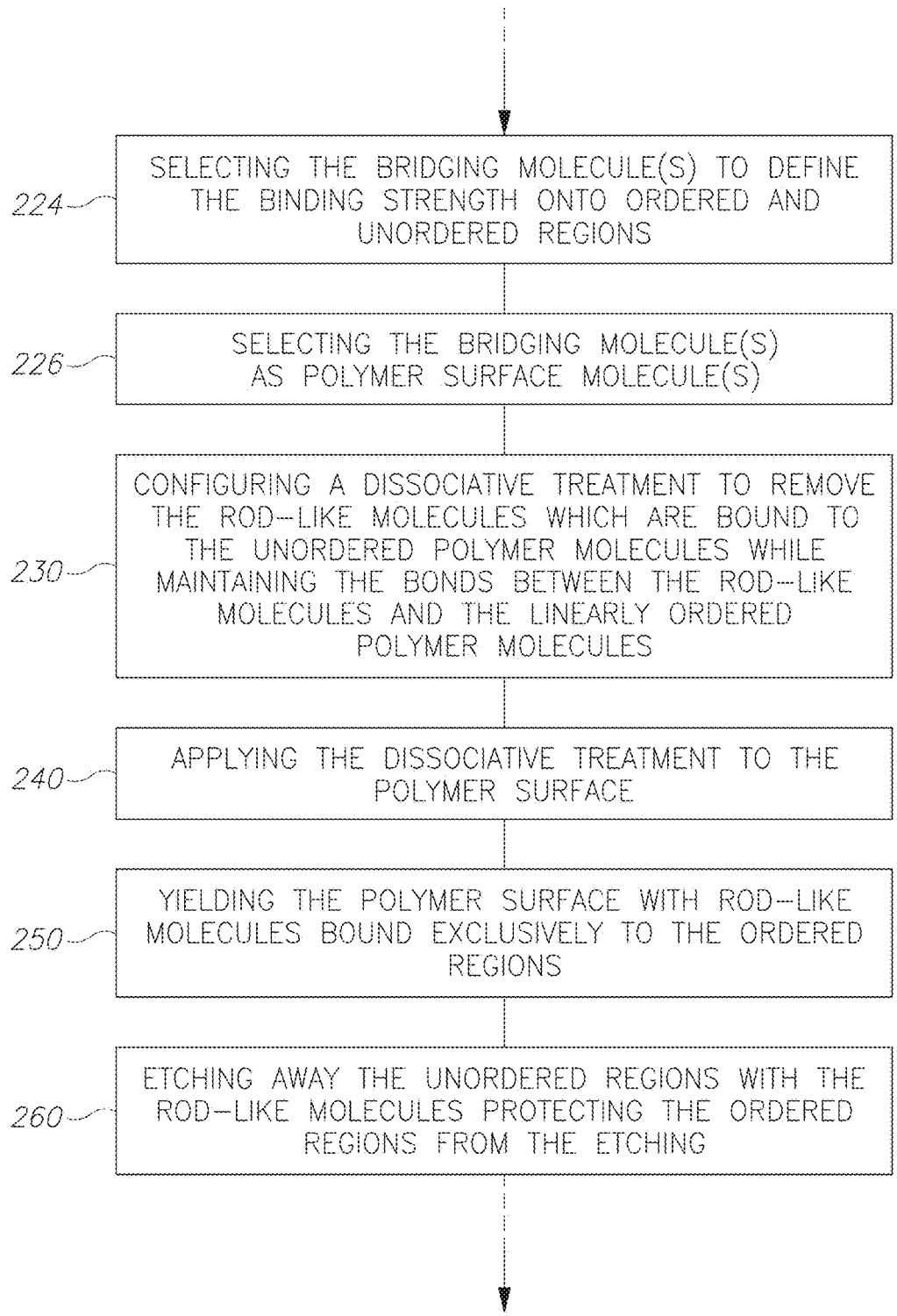
Figure 25 (cont. 1)

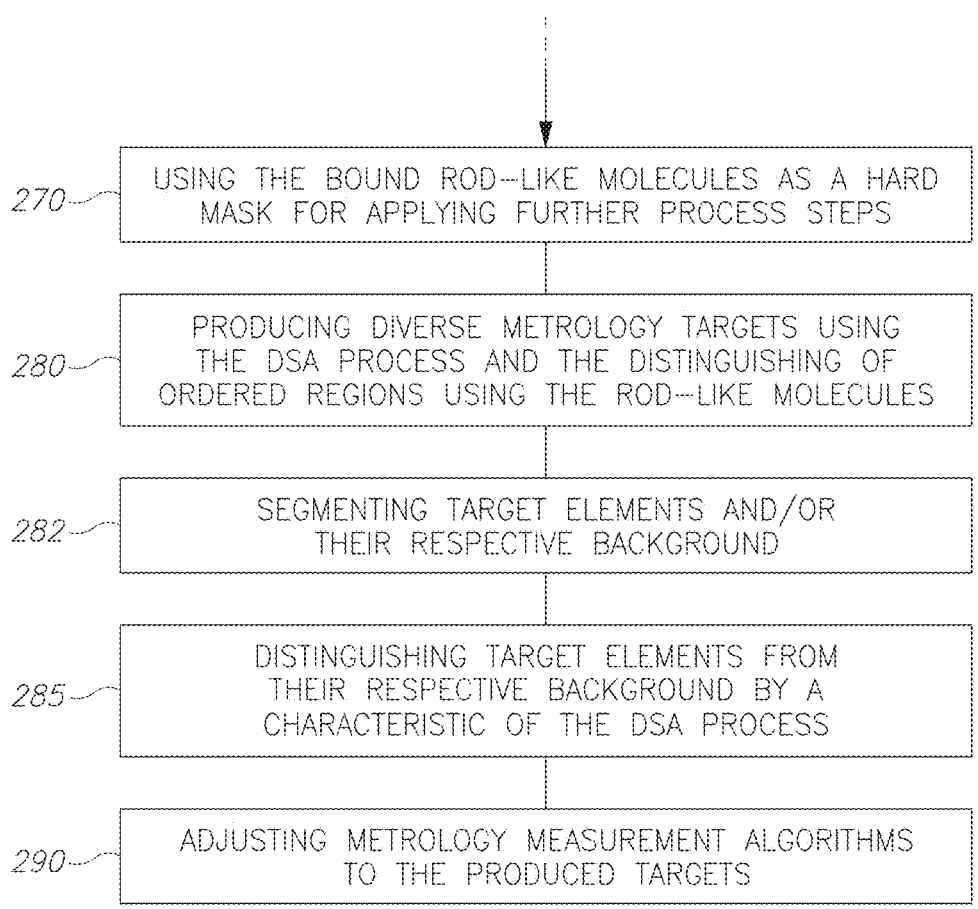
Figure 25 (cont. 2)

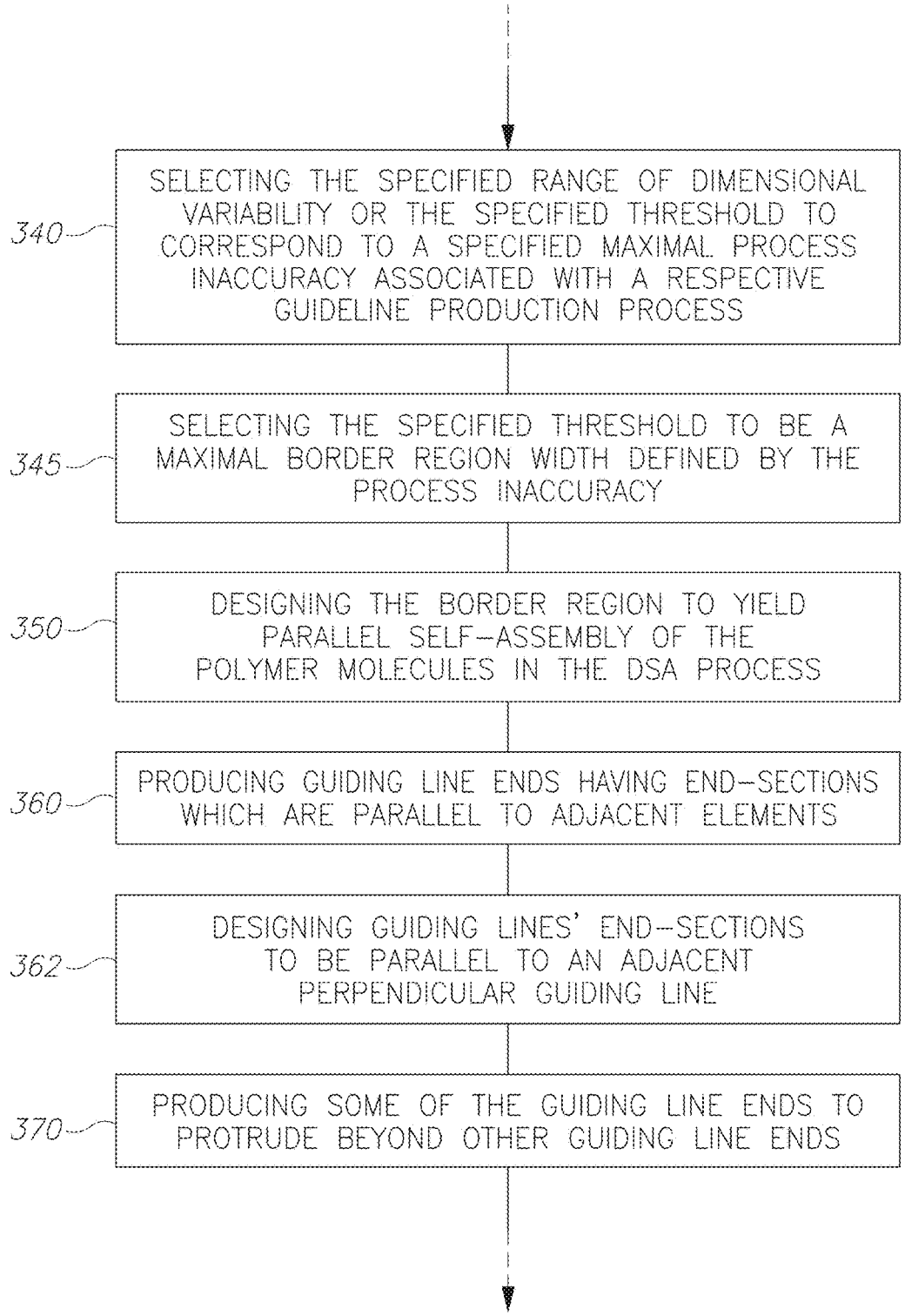
Figure 26 (cont. 1)

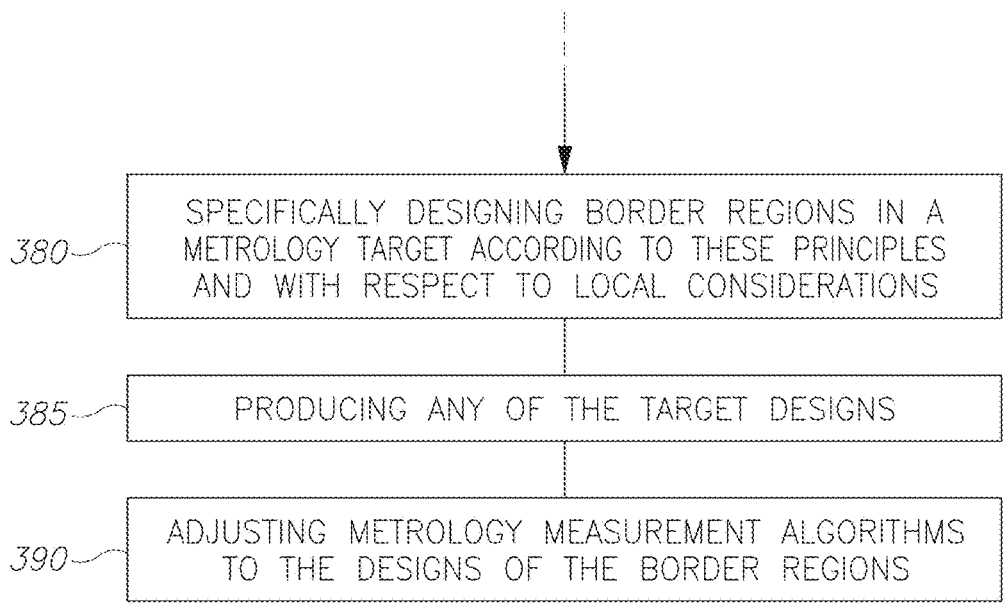
Figure 26 (cont. 2)

*400*

410 — DESIGNING A METROLOGY TARGET TO BE PRODUCED BY A DIRECTED SELF-ASSEMBLY (DSA) PROCESS

412 — DESIGNING AT LEAST ONE TARGET LAYER TO BE PRODUCED BY DSA

415 — DESIGNING ANY OF SCOL, AIM, AIMID AND BLOSSOM TARGETS AS DSA-BASED TARGETS

420 — PRODUCING A METROLOGY TARGET USING A DSA PROCESS

430 — DISTINGUISHING AT LEAST ONE TARGET ELEMENT FROM ITS BACKGROUND BY A CHARACTERISTIC OF THE DSA PROCESS

432 — SELECTING THE DSA CHARACTERISTIC AS ANY OF THE PRESENCE, THE DIRECTION, THE SPATIAL FREQUENCY AND THE DIMENSIONS OF THE GUIDELINES

435 — DISTINGUISHING TARGET ELEMENTS FROM THEIR RESPECTIVE BACKGROUND REGIONS THROUGH A DIRECTION OF DSA GUIDING LINES

440 — DISTINGUISHING TARGET ELEMENTS FROM THEIR RESPECTIVE BACKGROUND REGIONS BY SEGMENTING EITHER OR BOTH TARGET ELEMENTS AND THE RESPECTIVE BACKGROUND REGIONS

Figure 27

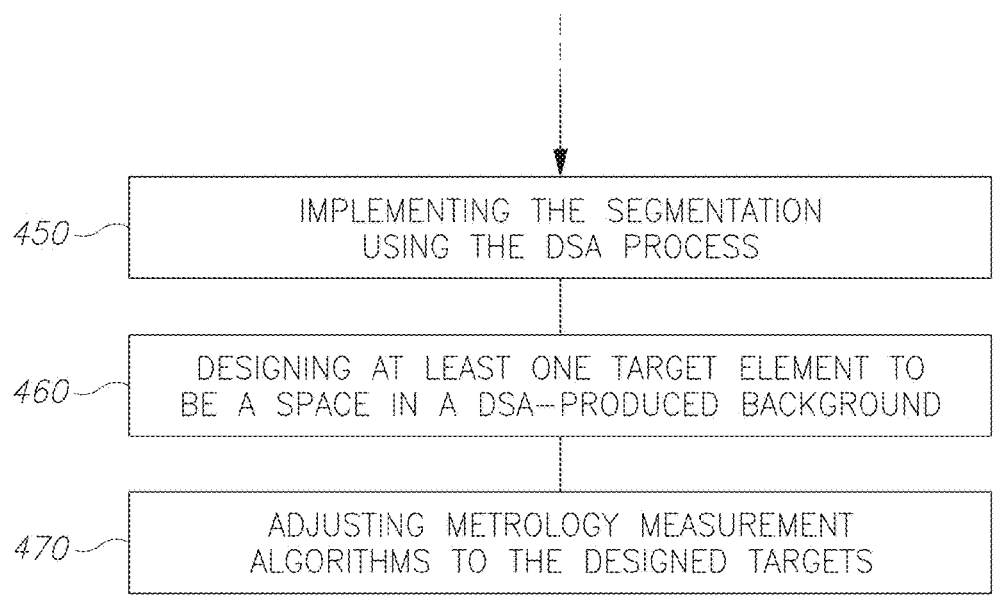
Figure 27 (cont. 1)

METHOD AND APPARATUS FOR DIRECT SELF ASSEMBLY IN TARGET DESIGN AND PRODUCTION

CROSS-REFERENCE TO RELATED APPLICATIONS

This application is a Continuation of International Patent Application Serial No. PCT/US2014/33621, filed on Apr. 10, 2014, which application claims priority of U.S. Provisional Patent Application No. 61/810,637, filed on Apr. 10, 2013, U.S. Provisional Patent Application No. 61/810,995, filed on Apr. 11, 2013, U.S. Provisional Patent Application No. 61/829,128, filed on May 30, 2013, and U.S. Provisional Patent Application No. 61/866,546, filed on Aug. 16, 2013, which applications are incorporated herein by reference.

FIELD OF THE INVENTION

The present invention relates to the field of metrology target design, and more particularly, to using the directed self-assembly (DSA) process for target design and production, with special focus on overlay target design and metrology.

BACKGROUND OF THE INVENTION

Metrology targets are designed to enable the measurement of parameters that indicate the quality of wafer production steps and quantify the correspondence between design and implementation of structures on the wafer. Metrology targets as specific structures optimize the requirements for device similarity and for optical measurability.

A directed self-assembly (DSA) process is used to create structures by directing a block co-polymerization process according to guiding lines which determine the spatial arrangement of the polymer blocks.

BRIEF SUMMARY OF THE INVENTION

One aspect of the present invention provides methods of designing metrology targets comprising distinguishing a target element from its background area by segmenting the background area, and respective targets. Segmenting may be achieved by a directed self-assembly (DSA) process, wherein at least one target element of the target is distinguished from its background by at least one characteristic of the DSA process. In one aspect of the present invention, producing two adjacent target structures by a DSA process, having a border region between the target structures that comprises a first guiding line of one of the target structures and a plurality of guiding line ends of respective guidelines of the other target structure, may comprise designing the guiding line ends at the border region to maintain a distance below a specified threshold to the first guiding line, upon producing the target elements with a width of the border region being up to a specified maximal process inaccuracy threshold associated with a respective guideline production process.

One aspect of the present invention provides a method comprising binding rod-like molecules onto a polymer surface which comprises ordered regions having linearly arranged polymer molecules and unordered regions in which polymer molecules are not linearly arranged, wherein the rod-like molecules are selected to bind to linearly arranged polymer molecules stronger than to polymer molecules which are not linearly arranged, and applying a dissociative treatment to the polymer surface with the bound rod-like molecules, configured to remove the rod-like molecules which are bound to the polymer molecules which are not linearly arranged while maintaining the bonds between the rod-like molecules and the linearly arranged polymer molecules, to yield the polymer surface with rod-like molecules bound exclusively to the ordered regions.

One aspect of the present invention provides a method of producing two adjacent target structures by a directed self-assembly (DSA) process, wherein a border region between a plurality of target structures includes a first guiding line of a first target structure, and a plurality of guiding line ends of respective guidelines of a second target structure, wherein designing the guiding line ends at the border region to maintain a distance below a specified threshold to the first guiding line, and producing the target elements with a width of the border region being up to a specified maximal process inaccuracy threshold associated with a respective guideline production process.

One aspect of the present invention provides a metrology target including a polymer surface which includes ordered regions having linearly arranged polymer molecules and unordered regions in which polymer molecules are not linearly arranged, and rod-like molecules bound onto the ordered regions, the rod-like molecules selected to bind to linearly arranged polymer molecules stronger than to polymer molecules which are not linearly arranged.

One aspect of the present invention provides a hard mask including rod-like molecules bound onto ordered regions of a polymer surface, wherein the polymer surface includes ordered regions having linearly arranged polymer molecules, and unordered regions in which polymer molecules are not linearly arranged and wherein the rod-like molecules are selected to bind to linearly arranged polymer molecules stronger than to polymer molecules which are not linearly arranged.

One aspect of the present invention provides a metrology target including at least one layer produced by a directed self-assembly (DSA) process, the at least one layer including at least one target element which is distinguished from a background associated with the at least one target element by at least one characteristic of the DSA process.

One aspect of the present invention provides a metrology target including at least two adjacent target structures produced by a directed self-assembly (DSA) process, wherein a border region between the target structures includes a first guiding line of one of the target structures, and a plurality of guiding line ends of respective guidelines of the other target structure and wherein the guiding line ends at the border region are designed to maintain a distance below a specified threshold to the first guiding line, upon producing the targets with a width of the border region being up to a specified maximal process inaccuracy threshold associated with a respective guideline production process.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIG. 25 is a high level flowchart illustrating methods, according to some embodiments of the invention;

DETAILED DESCRIPTION OF THE INVENTION

Figure 1:
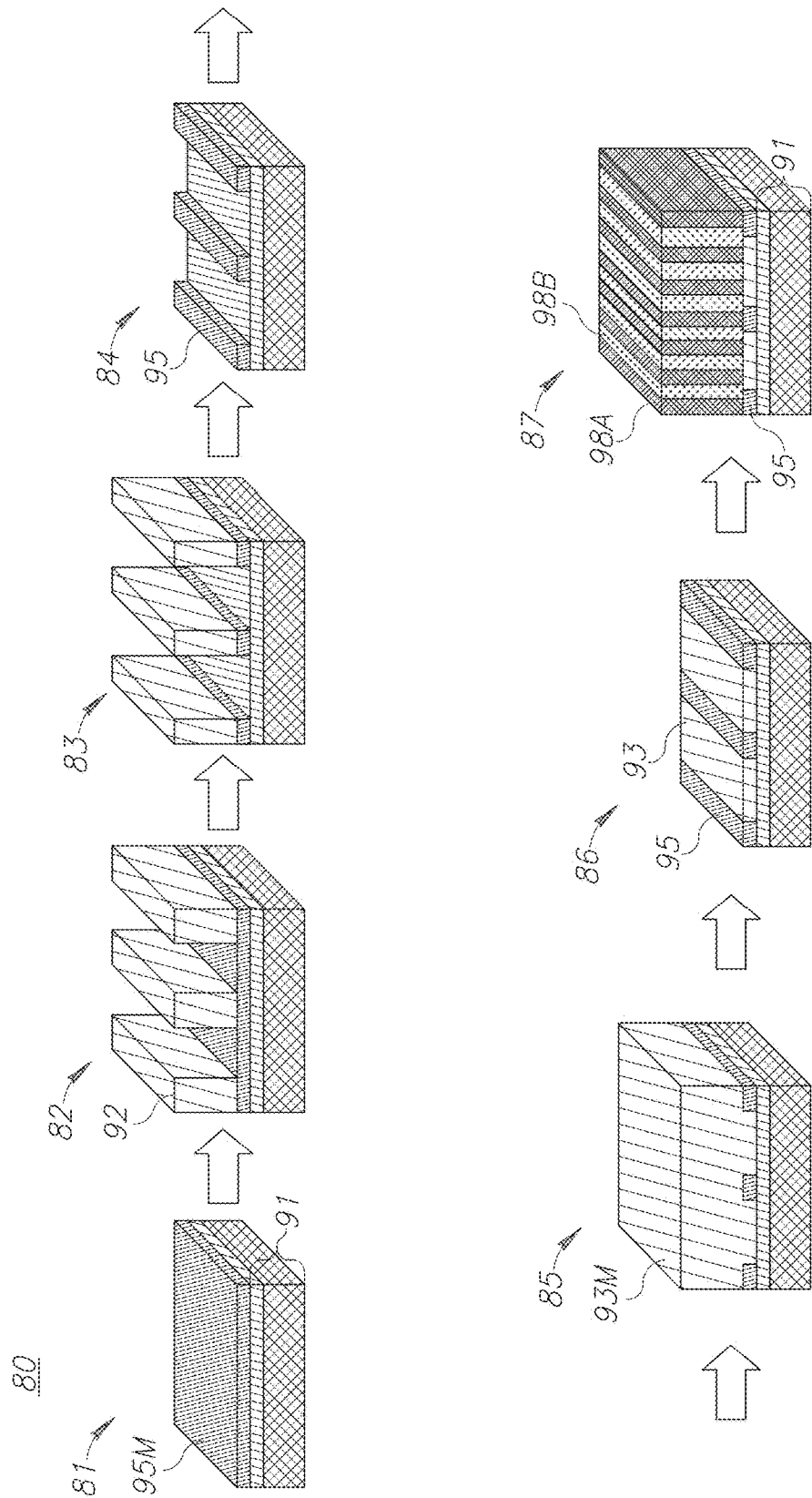
FIG. 1 is a high level schematic block diagram illustrating the production of structures using the directed self-assembly (DSA) process.

Prior to the detailed description being set forth, it may be helpful to set forth definitions of certain terms that will be used hereinafter.

The terms "metrology target" or "target" as used herein in this application, are defined as any structure designed or produced or a wafer which is used for metrological purposes. Non-limiting examples for metrology targets are imaging targets such as AIM (Advanced Imaging Metrology), BiB (Box-in-Box), AIMid and BLOSSOM and their corresponding variations and alternatives; and scatterometry targets such as SCOL (Scatterometry Overlay) and their corresponding variations and alternatives. The terms "metrology measurement" or "measurement" as used herein in this application, are defined as any metrology measurement procedure used to extract information from metrology targets. For example, metrology measurements may be imaging of the targets or scatterometry measurements of the targets. Non-limiting examples for metrology measurements include overlay measurement (imaging or scatterometry), critical dimension (CD) measurement, focus and dose measurement, etc.

The term "target structure" as used herein in this application, is defined as a part of a target, such as a target feature or a background feature. Target structures may be bar-like or area-like, e.g., in case of target features in AIM and AIMid target respectively, or be frame-like, enclosing other target structures, e.g., in case of the peripheral background of such targets.

The term "target element" as used herein in this application, is defined as a continuous element in a target structure, such as a segment or an unsegmented bar which is set within a background. The term "background" as used herein in this application, is defined as a wafer area proximate to a target element, which is distinguishable from the target element by design.

The term "segmentation" as used in this application refers to a sub-division of a target structure into smaller elements. Respectively, the term "segment" as used in this application refers to the smallest solid part or feature into which a target structure is segmented.

The term "guiding line" as used herein in this application, is defined as a designed line in any type of layer, which serves to direct polymerization in a DSA process. It is noted that the term "guiding line" refers to any type of guiding structure, under implementation of any type of DSA process (e.g., graphoepitaxy, chemoepitaxy). Specifically, guiding lines may be target elements themselves and/or serve to produce polymer patterns which are used as target structures or as a basis for producing target structures by further processing.

The terms "ordered", "unordered" and "disordered" as used herein in this application with respect to the polymer regions resulting from the DSA or other process, are defined as a level of order of the features in the regions, as a non-limiting example, the level of order of polymer lines produced by the DSA process. The differentiation between "ordered", "unordered" and "disordered" is qualitative, or may be defined precisely according to specified criteria. In the illustrated examples, these terms are used according to the graphical representation in FIG. 4A, ordered regions comprising only straight parallel polymer lines, disordered regions lacking continuous straight parallel patterns and unordered regions having incomplete but partly continuous straight parallel patterns. "Ordered" regions may comprise highly regular patterns other than parallel straight lines, for example, concentric circles. The respective unordered and disordered regions manifest different degrees of deviation from the respective regular patterns. The terms "unordered" and "disordered" are to some extent exchangeable, "disordered" generally denoting a lower level of order than "unordered". These terms are understood to apply in a broad sense to the level of order of lines on a surface of any kind, not only surfaces produced by the DSA process.

The term "rod-like molecules" as used herein in this application, is defined as molecules which are straight and stiff, having a long dimension and a short dimension and resisting form changing forces. The quantitative characteristics of the rod-like molecules are determined specifically with respect to the surface characteristics (e.g., types of DSA polymers and polymer line dimensions), the levels of order the rod-like molecules are used to distinguish and the required specified binding affinity of the rod-like molecules to ordered and unordered regions.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

FIG. 1 is a high level schematic block diagram illustrating the production of structures using the directed self-assembly (DSA) process. The structures may be part of device structure or of metrology targets. FIG. 1 schematically illustrates steps 80-86 of producing guide line 95 and the DSA step 87. In first step 81, guideline material 95M is attached to s substrate 91 (which may itself be composite and/or multilayered). For example, in a DSA process involving polystyrene (PS) and polymethylmethacrylate (PMMA) molecules, guideline material may be PS which is cross linked onto substrate 91. It is noted that while examples in the current disclosure relate to a PS-PMMA DSA process, these materials are not limiting the scope of the invention, the principles of which may be applied to other polymers and DSA systems as well. Step 82 is a lithographic step defining which guideline material 95M will be removed using mask 92, step 83 is an etching step in which guideline (and mask) material is removed to reach the designed guide line dimensions (e.g., by dry plasma etch) and step 84 is a resist removal step that results in the prepared guidelines. In the DSA process, guidelines 95 are designed to direct the polymerization of the DSA polymers to form a specified pattern.

Next, step 85 grafts material 93M onto substrate 91 to fill the spaces between guiding lines 95, e.g., using OH-Brush grafting, and guiding lines 95 are re-exposed in step 86 to present guiding lines 95 interspaced by grafts 93 which support the DSA polymerization process. At step 86, the guiding line pattern is ready for the actual application of the DSA process, resulting, at step 87, in fine and parallel polymer lines 98A, 98B formed by polymerization (possibly involving an annealing step) which is directed by guiding lines 95 (in the PS-PMMA DSA example, polymer lines 98A, 98B are PS and PMMA, respectively).

Figure 4A:
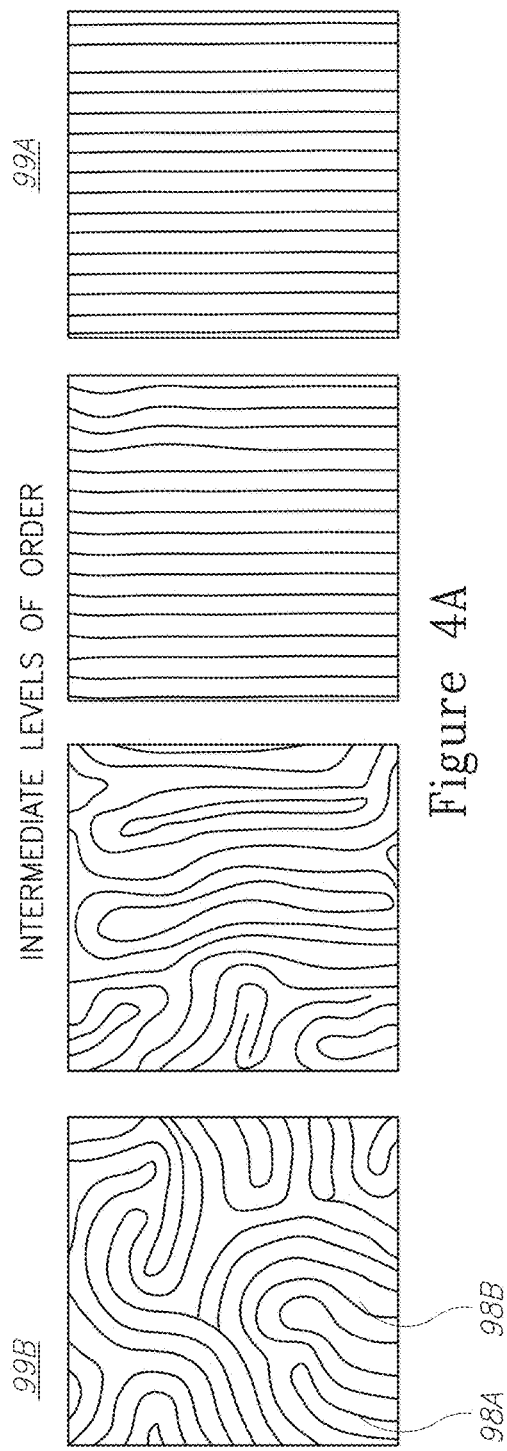
FIG. 4A is a schematic illustrating a range of order levels achieved by a DSA process.

Depending on the presence or absence of guiding lines 95, the orientations and pattern of polymer lines 98A, 98B may be highly ordered, unordered or have an intermediate level of order, as illustrated in FIG. 4A below. In particular, areas with regularly and closely spaced guiding lines 95 produced at correct locations yield regularly parallel polymer lines 98A, 98B. However, when guiding lines 95 are spaced otherwise, polymer lines 98A, 98B may be undulating as illustrated in step 87A in FIG. 2, or have different degrees of disorder (see FIG. 4A). In general, certain ordered regions 99A having correctly designed guiding lines may have highly ordered parallel polymer lines 98A, 98B, while other, unordered, regions 99B may have unordered or disordered polymer lines 98A, 98B by design or by lack of design.

Figure 2:
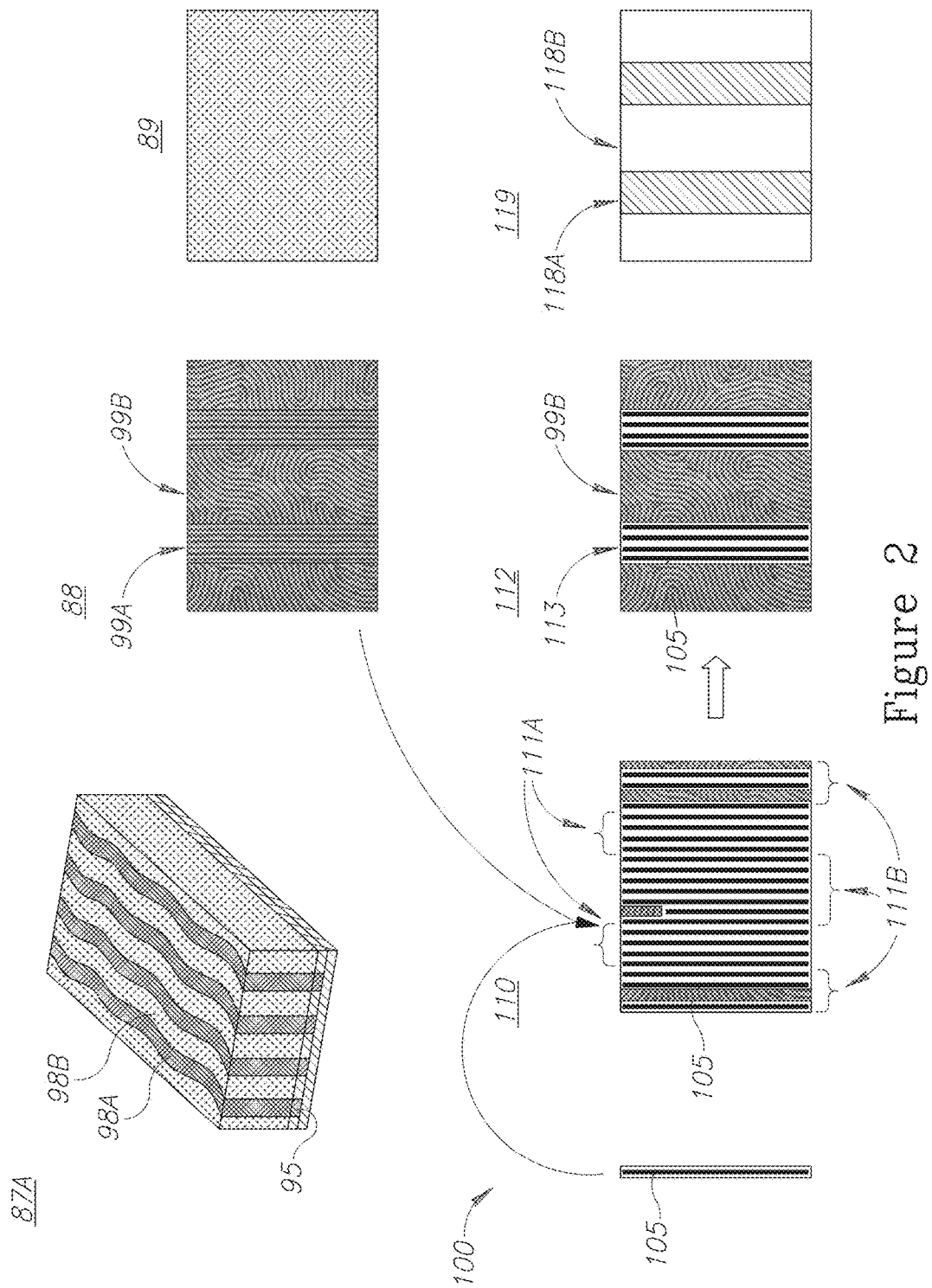
FIG. 2 is a high level schematic block diagram illustrating the enhancement of ordered regions on a DSA produced polymer surface, according to some embodiments of the invention.
Figure 3:
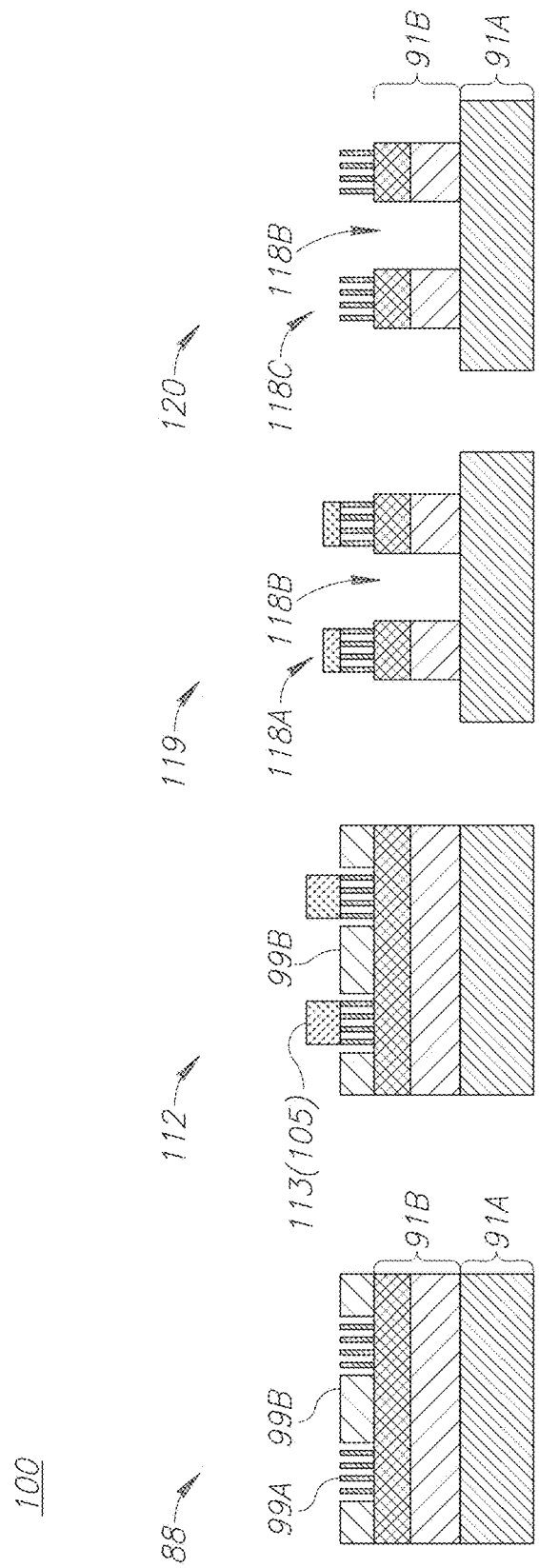
FIG. 3 is a high level schematic block diagram illustrating the enhancement of ordered regions on a DSA produced polymer surface, according to some embodiments of the invention.

FIGS. 2 and 3 are high level schematic block diagrams illustrating the enhancement of ordered regions 99A on a DSA produced polymer surface, according to some embodiments of the invention. The enhanced order regions may be used as a hard mask for consecutive production steps.

It is noted, that line thickness is constant and equal for both types of polymer lines 98A, 98B. Hence, a polymer surface 88 having ordered regions 99A and unordered regions 99B would exhibit a uniform optical image 89 lacking any details because layer details are too fine to be resolved and imaged, and the average illumination level is equal for ordered regions 99A and unordered regions 99B, i.e., no contrast exists between them. It is a metrology challenge to distinguish between the ordered and random areas 99A, 99B, respectively. If the inspection wavelength is much larger than the typical pattern pitch (which is in the order of the node, ~20 nm) the area looks uniform and grey (89). This is the typical case for optical metrology using a minimal wavelength that is at least an order of magnitude larger than the pattern pitch.

A method to enhance the measurement sensitivity is illustrated in steps 110, 112, 119 in FIGS. 2 and 3, illustrated in a top view and in a side view, respectively. To distinguish order and unordered regions 99A, 99B optically, an additional layer is deposited (step 100) on top of the patterned polymer surface. This layer is composed of molecules 105 which are rigid-rods, i.e., long and rigid straight lines (long compared to the pattern pitch), and bind selectively to ordered regions 99A, or at least bind stronger to ordered regions 99A than to unordered regions 99B. Upon imaging bound molecules 105 (after or without additional treatment to molecules 105 and/or to exposed unordered regions) a clear distinction can be made between regions 118A (resulting from ordered regions 99A) and 118B (resulting from unordered regions 99B) as they are well contrasted and larger than the resolution limit (119).

Certain embodiments comprise a metrology target comprising the polymer surface which comprises ordered regions 99A having linearly arranged polymer molecules and unordered regions 99B in which polymer molecules are not linearly arranged, and rod-like molecules 105 bound onto ordered regions 99A, rod-like molecules 105 selected to bind to linearly arranged polymer molecules stronger than to polymer molecules which are not linearly arranged. Unordered regions 99B of the target may be at least partly etched away with rod-like molecules 105 protecting ordered regions 99A from the etching. In certain embodiments, ordered and unordered regions 99A, 99B respectively may differ or may be made to differ topographically. The polymer surface may be produced by a DSA process and rod-like molecules 105 may comprise at least one of: cellulose, nanotubes (e.g., carbon, boron nitride, silicon, etc.) and rigid-rod polymers (e.g., poly ethylene terephthalate (PET), p-phenylene sulfonic acids, etc.). Rod-like molecules 105 may comprise cellulose molecules configured to have a crystalline form which depends upon a level of order on the bound region. Rod-like molecules 105 may comprise bridging molecules selected to define a relation between the binding affinity of rod-like molecules 105 to the polymer surface and the level of molecular order of the polymer surface.

In certain embodiments, at least one of rod-like molecules 105 and the polymer surface may be configured to enable distinction between rod-like molecules 105 and unordered regions 99B using polarized light. In certain embodiments, some or all rod-like molecules 105 may be used for metrology measurements or certain production steps and be removed thereafter. Rod-like molecules 105 may thus be used only or mainly for enhancing the metrology measurements without disturbing the integrated circuit production process. Rod-like molecules 105 may be selected or configured to provide an ability to optically distinguish them.

Certain embodiments comprise a hard mask comprising rod-like molecules 105 bound onto ordered regions 99A of the polymer surface, wherein the polymer surface comprises ordered regions 99A having linearly arranged polymer molecules and unordered regions 99B in which polymer molecules are not linearly arranged. Rod-like molecules 105 may be selected to bind to linearly arranged polymer molecules stronger than to polymer molecules which are not linearly arranged. The polymer surface may be produced by a DSA process and rod-like molecules 105 may comprise at least one of: cellulose, nanotubes and rigid-rod polymers. The rod-like molecules may comprise cellulose molecules configured to have a crystalline form which depends upon a level of order on the bound region.

Molecules 105 may exhibit selective bonding to the surface: molecules 105 may be selected to be attracted to one of the phases according to level of order, orientation or composition. For example, molecules 105 may be selected to bind to ordered regions 99A stronger than to unordered regions 99B. In another example, molecules 105 may be selected to be attracted to lines 98A and/or 98B and to fail to bind or to bind poorly to the lines when they wind. Selective bonding may have high sensitivity to the surface topography (e.g., in case of deposition over an already etched area) which may result to be different or be manipulated to differentiate between regions 99A, 99B.

Rod-like molecules 105 may be based on the cellulose molecule which may be formed as a long and rigid linear molecule, tending to form hydrogen bonds which allow it to bond to specific compounds and provide thereby the required material bonding selectivity. Cellulose rod-like molecules 105 may assemble to different induced crystalline cellulose phases, depending on the degree of order of the regions they bind to. Cellulose rod-like molecules 105 may be selected to have cellulose phases that react differently to solvents, and by dissolving only the phase which does not overlap the ordered phase to which it is bound, the required separation may be achieved. Additional chemical and mechanical steps may be used to achieve the phase separation, such as several depositing and cleaving steps.

Rod-like molecules 105 such as cellulose may be selected to provide the selective bonding in relation to the level order as well as the rigidity of the molecules that supports alignment of the molecules in ordered regions 99A. Other molecules may be attached as side changes to rod-like molecules 105, e.g., glucose units in the case of cellulose, which may act as bridging molecules to the surface, and exhibit the bonding selectivity to the wafer surface and/or as bridging molecules between adjacent rod-like molecules 105 that stabilize structures bound to linear regions. For example, a molecule combining cellulose and one of the two block polymers which were used to form the original DSA pattern layer (e.g., PS or PMMA) as bridging molecules may be used.

Upon application to the polymer surface, rod-like molecules 105 bind well to ordered regions 99A and form a layer 111A of rod-like molecules 105 thereupon (step 110). Rod-like molecules 105 may also bind to unordered regions 99B or parts thereof, and may form a weakly bound and non-uniform layer 111B thereupon (possibly with spaces within layer 111B), which then undergoes a dissociative treatment, i.e., separated and removed chemically, mechanically (e.g., polishing or shaking) using electromagnetic radiation (e.g., illumination with specified wavelengths), by application of heat or by any combination thereof. As the bonding quality of molecules 105 and layers 111A, 111B depend on the surface pattern level of order, molecules 105 that are weakly bound may be removed, for example by applying equal attractive forces on all molecules which is between the binding strength of rod-like molecules 105 to ordered regions and the binding strength of rod-like molecules 105 to unordered regions. The geometrical form and dimensions of rod-like molecules 105 may be selected to enhance the bonding selectivity.

As a result of the selective bonding and the optional dissociative treatment, distinct patterns 113 of rod-like molecules 105 are formed according to the locations of ordered regions 99A (step 112). Unordered regions 99B between patterns 113 may be left on or removed. Upon imaging of the prepared element 112, a distinct image 119 of elements 118A corresponding to pattern 113 can be resolved from a background 118B corresponding to unordered regions 99B that do not have rod-like molecules 105 bound thereto. Comparing image 119 with image 89 illustrates the achieved contrast between ordered and unordered regions 99A, 99B respectively. Image 119 is also understood as a lower resolution illustration of the density of rod-like molecules 105, which illustrates the clear phase separation between the order and unordered regions 99A, 99B respectively. Measurement of the properties of molecule patterns 113, such as alignment to previous layers and width, reflects the same properties of order regions 99A of the underlying layer. Once the measurement is done, the rod-like molecules may be removed, and thus be used only for enhancing the metrology measurements without disturbing the integrated circuit production process.

Patterns 113 may also be used as a hard mask, attached to the wafer element, to apply further patterning processes to wafer areas distinguished by hard mask 113. For example, regions 99B that are not covered by hard mask 113 may be etched, grafted, illuminated, have material layers grown upon, etc. according to device or target designs. This concept is useful and may be applied not only for the metrology target formation but also for the integrated circuit production process.

Pattern 113 may also be used as a resist layer in cut processes of the underlying layer since layer 113 in region 118A is perfectly aligned to the one beneath it (99A). This enables more accurate patterning (e.g., to implement a "self-aligned" cut layer which is aligned with the underlying pattern). An example for such process is plotted in FIG. 3, which illustrates the process from a side view. Images or steps 88, 112 and 119 correspond in FIGS. 2 and 3. Substrate 91 is illustrated to comprise several layers, denoted by the numerals 91A and 91B. Step 119 in FIG. 3 comprises an etching away of part 91B of substrate 91 using pattern 113 as a hard mask that protects sections of part 91B which are under rod-like molecules 105 that are bound to ordered regions 99A. The etching step may be selective etching and may comprise applying one or more etchings which does not affect significantly the hard mask 113 (which may be seen as a protective adhesive layer 113). The process may further comprise cleaning hard mask 113 (for example by chemical wash) to resolve in structure 120. The disclosed steps may be applied in a wide range of production processes related to various integrated circuit elements as well as metrology targets, for example to implement self-aligned elements which form according to the level of order in the underlying layer.

Advantageously, the method comprises deposition of an order selective layer which has selective bonding to the order regions; removal of the poor bonding quality parts of the order selective layer in order to transfer the pattern to the adsorbed layer (rather than to the layers below); using the pattern of the new layer in order to measure properties of the original layers; removing the pattern or using the pattern of the new layer for lithography steps; and using the new layer as part of the target design and for the integrated circuit production process.

A method 200 may comprise binding rod-like molecules onto a polymer surface which comprises ordered regions having linearly arranged polymer molecules and unordered regions in which polymer molecules are not linearly arranged, wherein the rod-like molecules are selected to bind to linearly arranged polymer molecules stronger than to polymer molecules which are not linearly arranged, and applying a dissociative treatment to the polymer surface with the bound rod-like molecules, configured to remove the rod-like molecules which are bound to the polymer molecules which are not linearly arranged while maintaining the bonds between the rod-like molecules and the linearly arranged polymer molecules, to yield the polymer surface with rod-like molecules bound exclusively to the ordered regions. Method 200 may comprise etching away the unordered regions with the rod-like molecules protecting the ordered regions from the etching. Prior to the binding of the rod-like molecules onto the polymer surface, method 200 may comprise any of producing the polymer surface by a directed self-assembly (DSA) process, at least partly etching the unordered regions, and creating topographical differences between the ordered and the unordered regions. Method 200 may comprise selecting the rod-like molecules to comprise cellulose, nanotubes and/or rigid-rod polymers. The linearly arranged polymer molecules may be associated with metrology target elements and method 200 may further comprise deriving an optical measurement signal from the yielded polymer surface with rod-like molecules bound exclusively to the ordered regions. Deriving the optical measurement signal may be carried out using polarized light configured to distinguish the bound rod-like molecules from the unordered regions. Method 200 may further comprise configuring at least one of the rod-like molecules and the polymer surface to enable distinction between the rod-like molecules and the unordered regions using polarized light. In certain embodiments, method 200 may further comprise removing the rod-like molecules bound exclusively to the ordered regions after the deriving of the optical measurement signal. A computer program product comprising a computer readable storage medium having computer readable program embodied therewith may be provided. The computer readable program configured to carry out metrology measurements of targets produced according to method 200. See further stages of method 200 in FIG. 25 below. Design and production elements and steps involved in distinguishing ordered regions from unordered regions and in producing and using the described hard masks may be incorporated to design and production of any of the designs of metrology targets 140 that are illustrated below.

FIG. 4A schematically illustrates a range of order levels achieved by a DSA process. FIG. 4A illustrates unordered and disordered polymer lines 98A, 98B as black and white lines (respectively) on images of actual polymer surfaces produced in a DSA process, with the black lines 98A corresponding to PS and white lines 98B corresponding to PMMA. These depictions are used in the application to illustrate the levels of order, e.g., near guide line edges (see below). They are used for exemplary illustrative purposes only, and are not to be understood as limiting the scope of processes, materials and dimensions to which the present invention is applicable. The dimensional proportions of the lines and spaces in FIG. 4A are arbitrary, non-limiting and are process-dependent. For example, lines 98A and spaces 98B may have similar widths and represent PS and PMMA lines produced by the DSA process, respectively. FIG. 4A illustrates four levels or order, namely ordered regions 99A, disordered regions 99B and regions with intermediate levels of order in between. Qualitatively, the left-most image is referred to as disordered and the right-most image is referred to as ordered. However, as different levels of order may be relevant for specific applications, no limitation is posed on the exact degree of order, to which the terms "ordered" and "unordered" refer, but these are defined by specific requirements. Accordingly, the bonding affinity of rod-like molecules 105 may be selected to be high for ordered regions and lower or null for unordered regions, wherein the exact values are adapted to the specific levels of order derived from specific applicative requirements.

Figure 4B:
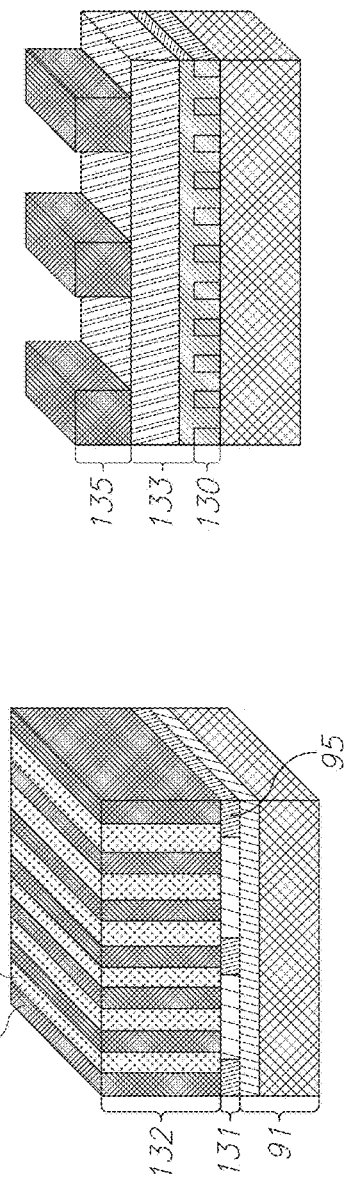
FIG. 4B is a high level schematic block diagram illustrating the production of two target layers by the DSA process, according to some embodiments of the invention.

FIG. 4B is a high level schematic block diagram illustrating the production of two target layers by the DSA process, according to some embodiments of the invention. Similar production principles may be used to generate multi-layered targets. DSA layers may be produced as any one, as several or as all layers in the target. In FIG. 4B, a DSA layer as a previous (bottom) layer 130 is illustrated, with a current layer 135 not necessarily produced by a DSA process (alternatively, substrate 91 may comprise a bottom layer, and the layer produced in step 87 may be the target's upper layer). At step 87, a guiding line layer 131 with guiding lines 95 (set on substrate 91) is used to produce a DSA layer 132 having polymer lines 98A, 98B, which is then further processed (e.g., cut, etched, covered with other layer 133, etc.) to yield previous layer 130 in step 127. Upon covering layer 133 or directly upon layer 130, a current layer 135 of the metrology target is deposited. It is noted that throughout the disclose, the previous (bottom) layer is referred to with the numeral 130 and the current (top) layer is referred to with the numeral 135, irrespective whether they were produced by a DSA process or not.

Figure 5A:
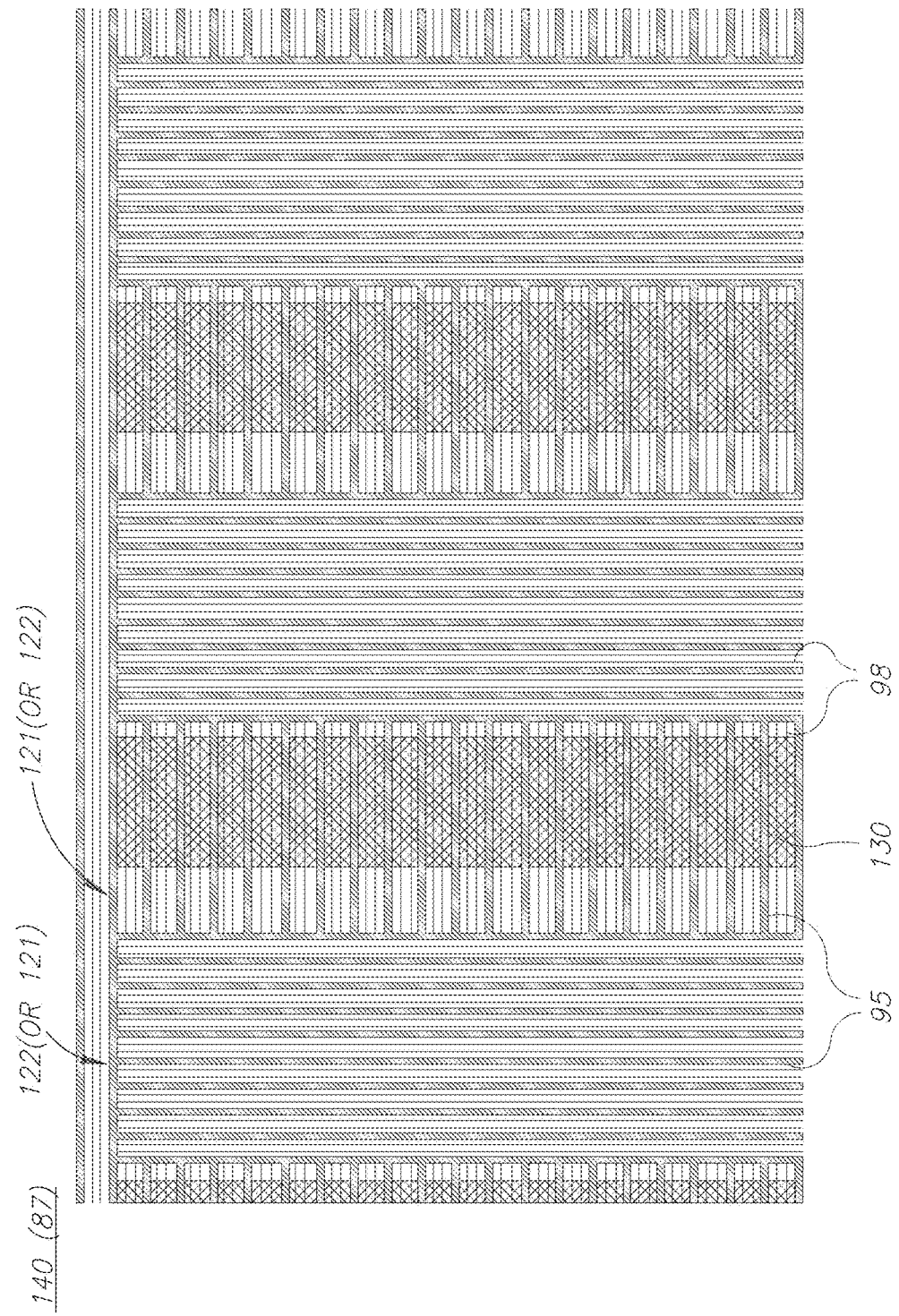
FIG. 5A is a high level schematic illustration of exemplary bar-type targets produced using the DSA process, according to some embodiments of the invention.
Figure 5B:
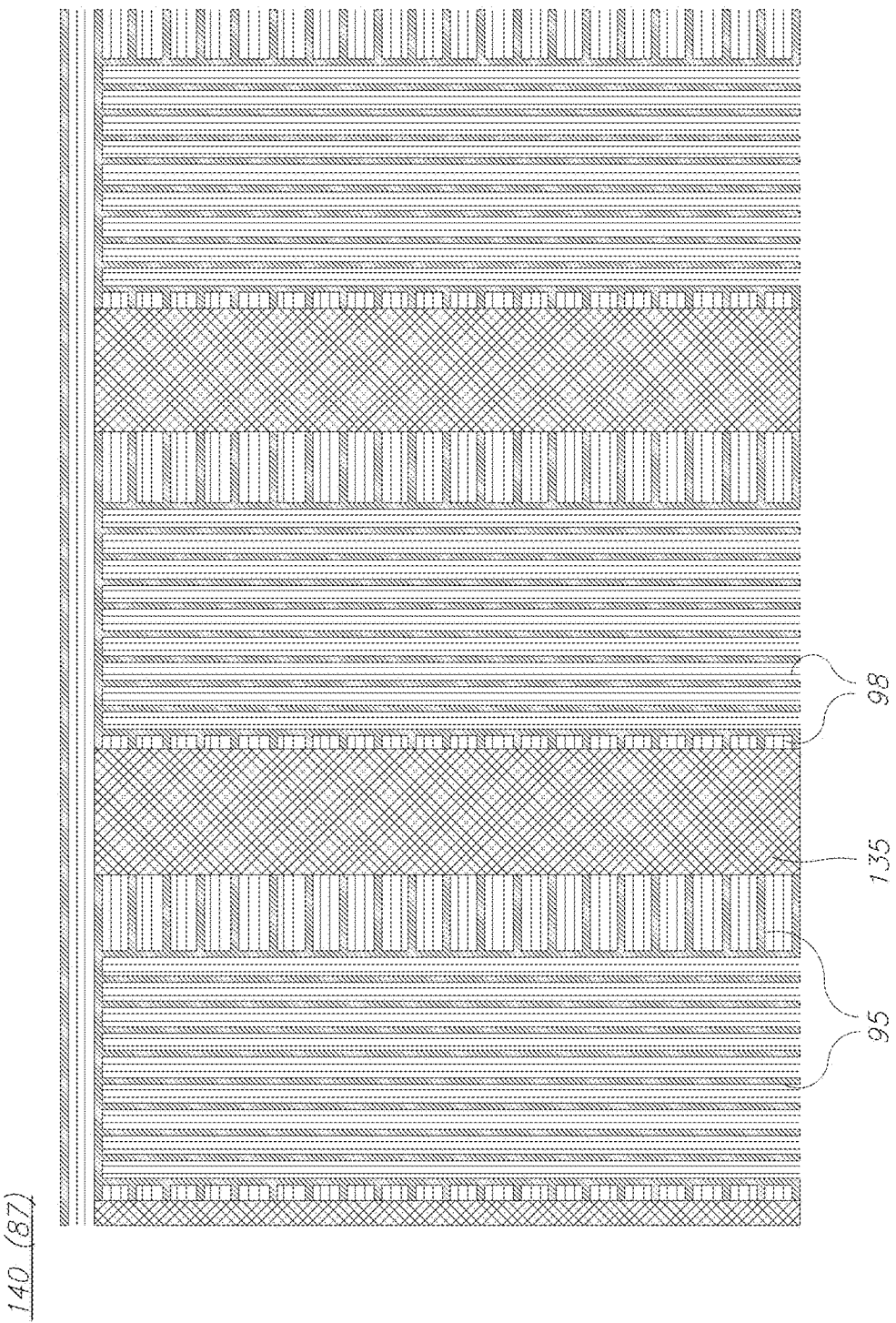
FIG. 5B is a high level schematic illustration of exemplary bar-type targets producced using the DSA process, according to some embodiments of the invention.

FIGS. 5A and 5B are high level schematic illustrations of exemplary bar-type targets 140 produced using the DSA process, according to some embodiments of the invention. The design principles are applicable, e.g., to SCOL and AIM targets. FIG. 5A schematically illustrates target 140 having the DSA layer as current layer 135 while FIG. 5B schematically illustrates target 140 having the DSA layer as previous layer 130. The respective previous layer 130 in FIG. 5A and current layer 135 in FIG. 5B are cross-hatched to distinguish them from guidelines 95 and polymer lines 98 which are schematically indicated as thick and thin lines, respectively. However, respective previous layer 130 in FIG. 5A and current layer 135 in FIG. 5B may also be produced using a respective DSA process, and these layers may be likewise segmented, and are hence not limited by the hatching to refer to bulk bars.

The number and dimensions of guidelines 95 and polymer lines 98 are selected according to specific target and process requirements, and are not limited to the patterns illustrated in FIGS. 5A and 5B. The direction of guidelines 95 defines the direction of polymer lines 98 and is used to differentiate target elements 122 from their background regions 121. Any orientation may be selected for either, as illustrated in FIG. 5A. Additionally or alternatively, the DSA process parameters may differ between target elements 122 and background 121, for example, guideline size, density or spacing may change to yield a difference in the produced polymer layer.

Metrology targets 140 illustrated in the present disclosure may comprise at least one target element on a segmented background, wherein the at least one target element may be unsegmented or segmented differently than its background. The segmentation of either or both target elements and their background may be achieved using a DSA process or a different process. Different segmentation of different target elements and/or different background regions may be achieved by different production methods or by different DSA process parameters. The differences in segmentation between the at least one target element and its background may be with respect to, e.g., segmentation pitch, feature size, spatial frequency, orientation of segmentation, aspect ratio, topography, duty cycle and segmentation pattern. The segmentation, including in embodiments the parameters of the DSA process, of the at least one target element and its background may be configured to reduce an unwanted global etch bias, a local etch bias, a polish bias, a film thickness bias and/or a lithographic print bias below a specified threshold. The segmentation and particularly guidelines 95 may be produced using design rules which are compatible with a lithographic process, an etch process, a polish process and/or a thin film deposition process. At least one of the target element and its background may be rastered or comprise device features. In certain embodiments, all transitions between target features and adjacent background features may be designed to maintain a feature size of the features below 300 nm or below 100 nm. Respective methods of designing and measuring metrology targets comprise distinguishing a target element from its background area by segmenting the background area and measuring the respective distinguishing features.

Figure 6A:
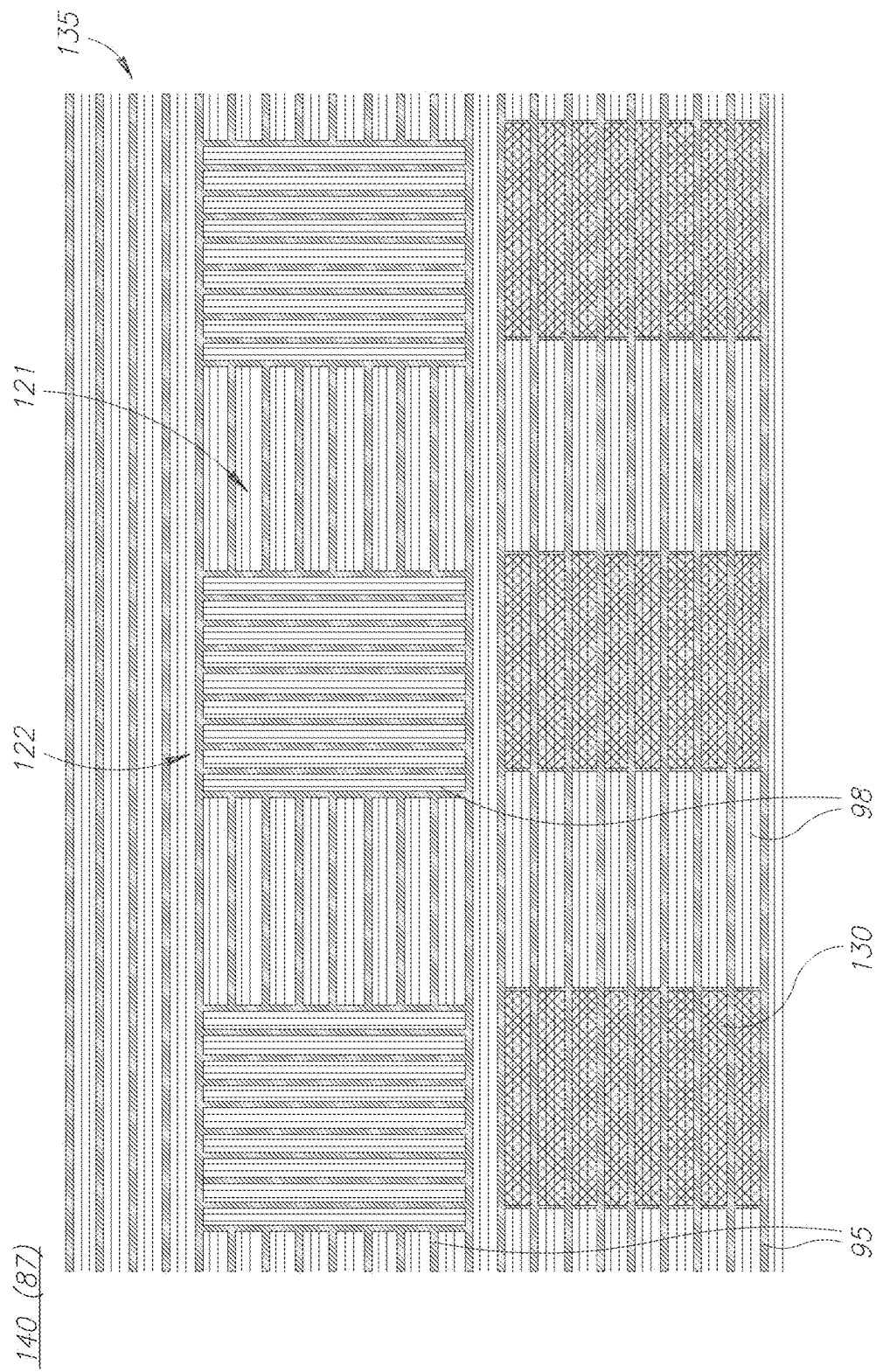
FIG. 6A is a high level schematic illustration of exemplary area-type targets produced using the DSA process, according to some embodiments of the invention.
Figure 6B:
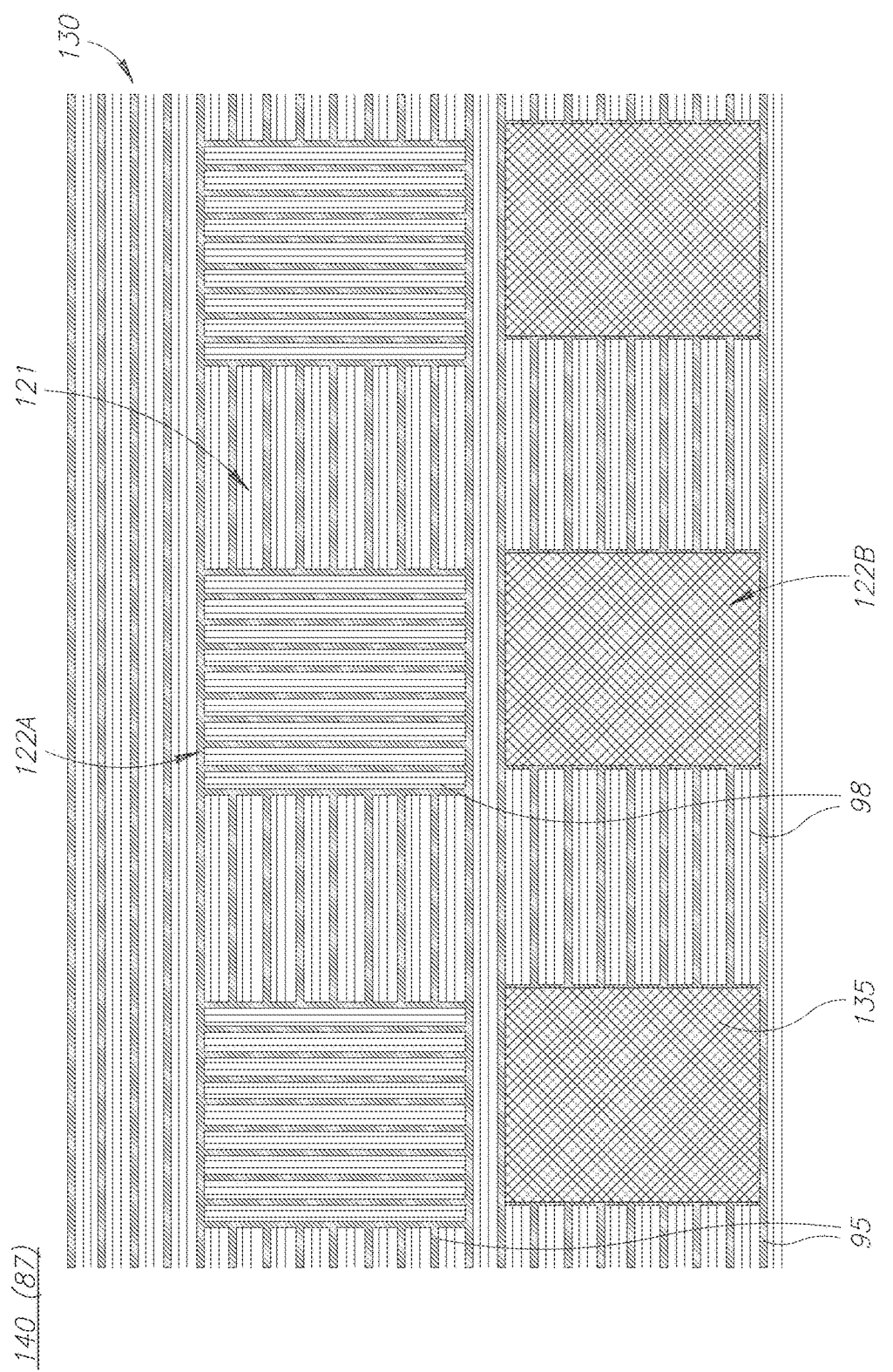
FIG. 6B is a high level schematic illustration of exemplary area-type targets produced using the DSA process, according to some embodiments of the invention.

FIGS. 6A and 6B are high level schematic illustrations of exemplary area-type targets 140 produced using the DSA process, according to some embodiments of the invention. The design principles are applicable, e.g., to BLOSSOM, BiB and AIMid targets.

FIG. 6A schematically illustrates target 140 having the DSA layer as current layer 135 while FIG. 6B schematically illustrates target 140 having the DSA layer as previous layer 130. The respective previous layer 130 in FIG. 6A and current layer 135 in FIG. 6B are cross-hatched to distinguish them from guidelines 95 and polymer lines 98 which are schematically indicated as thick and thin lines respective. However, respective previous layer 130 in FIG. 6A and current layer 135 in FIG. 6B may also be produced using a respective DSA process, and these layers may be likewise segmented, and are hence not limited by the hatching to refer to bulk areas.

The number and dimensions of guidelines 95 and polymer lines 98 are selected according to specific target and process requirements, and are not limited to the patterns illustrated in FIGS. 6A and 6B. The direction of guidelines 95 defines the direction of polymer lines 98 and is used to differentiate target elements 122 from their background regions 121. Any orientation may be selected for either. Additionally or alternatively, the DSA process parameters may differ between target elements 122 and background 121, for example, guideline size, density or spacing may change to yield a difference in the produced polymer layer.

Figure 7A:
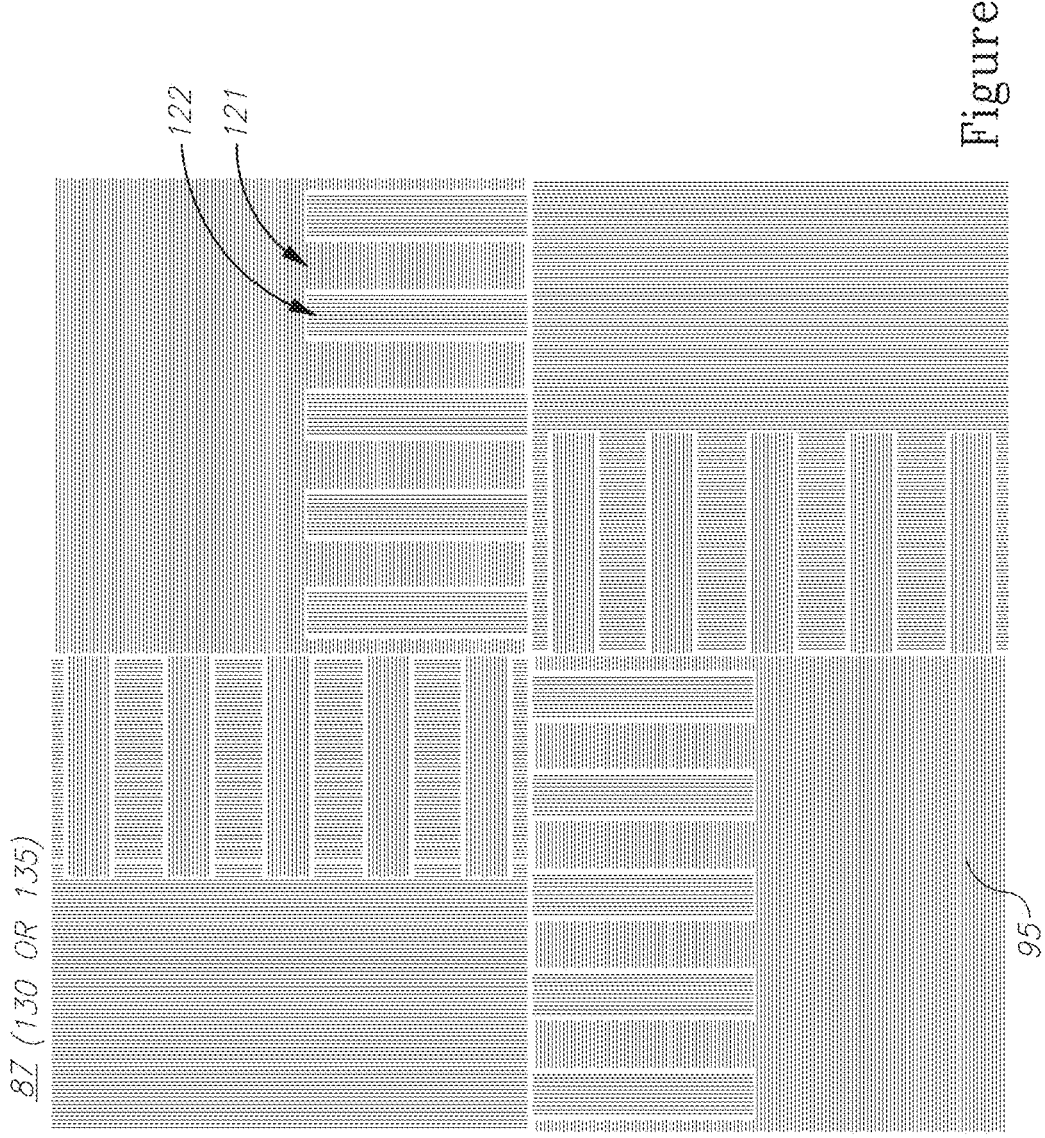
FIG. 7A is a high level schematic illustration of exemplary AIM targets produced using the DSA process, according to some embodiments of the invention.
Figure 7B:
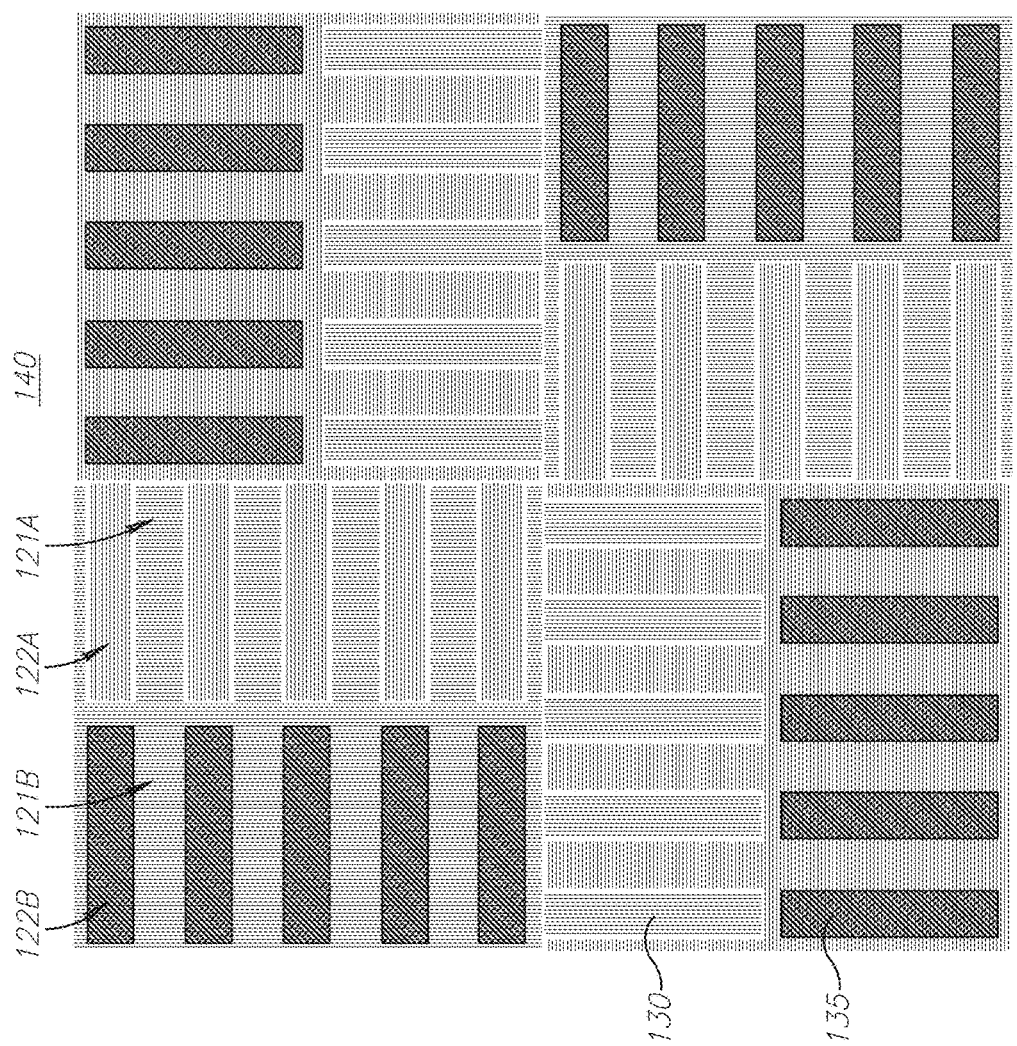
FIG. 7B is a high level schematic illustration of exemplary AIM targets produced using the DSA process, according to some embodiments of the invention.

FIGS. 7A and 7B are high level schematic illustrations of exemplary AIM targets produced using the DSA process, according to some embodiments of the invention. FIG. 7A schematically illustrates one layer in such target, possibly either or both previous layer 130 or current layer 135, as produced by the DSA process at step 87. The layer comprises target elements 122 and background 121 which may be uniform over the whole layer or over parts of the layer (quadrants in the illustrated example). Background 121 may further comprise regions onto which or below which target elements of different layers are produced. FIG. 7B schematically illustrates a two-layered target, in which the layer illustrated in FIG. 7A is the previous layer (having target elements 122A and background regions 121A), and hatched bars as target elements 122B on background 121B (which may be segmented, similar or different from background 121A). Target elements 122B may be solid or segmented, and may likewise be produced in a DSA process.

A method 400 may comprise producing a metrology target by a directed self-assembly (DSA) process, wherein at least one target element of the target is distinguished from its background by at least one characteristic of the DSA process, such as a direction of DSA guiding lines. Metrology targets 140 comprise at least one layer produced by the DSA process and comprising at least one target element which is distinguished from its background by at least one characteristic of the DSA process such as a direction of DSA guiding lines. The metrology target may be of any type, e.g., SCOL, AIM, AIMID, BLOSSOM, BiB. Any layer of the target may be produced by the DSA process and any relative line orientation may be used. The at least one characteristic of the DSA process may be configured to provide an optical distinction between the at least one target element and its background, and method 400 may further comprise measuring the optical distinction. The optical distinction and the measuring may be carried out using polarized light. Features of the DSA-produced metrology target may be removed after the measuring. The at least one characteristic of the DSA process may be selected to enable distinction between the at least one target element and its background using polarized light and the measuring may be carried out using polarized light. A computer program product comprising a computer readable storage medium having computer readable program embodied therewith is provided, in which the computer readable program is configured to design and/or optimize metrology targets which are compatible with method 400. A computer program product comprising a computer readable storage medium having computer readable program embodied therewith is provided, in which the computer readable program is configured to carry out metrology measurements of targets produced according to method 400 and/or optimize them. See further stages of method 400 in FIG. 27 below. Design and production elements and steps regarding DSA production of target elements may be incorporated to design optimization and production of any of the designs of metrology targets 140 that are illustrated below.

Figure 8:
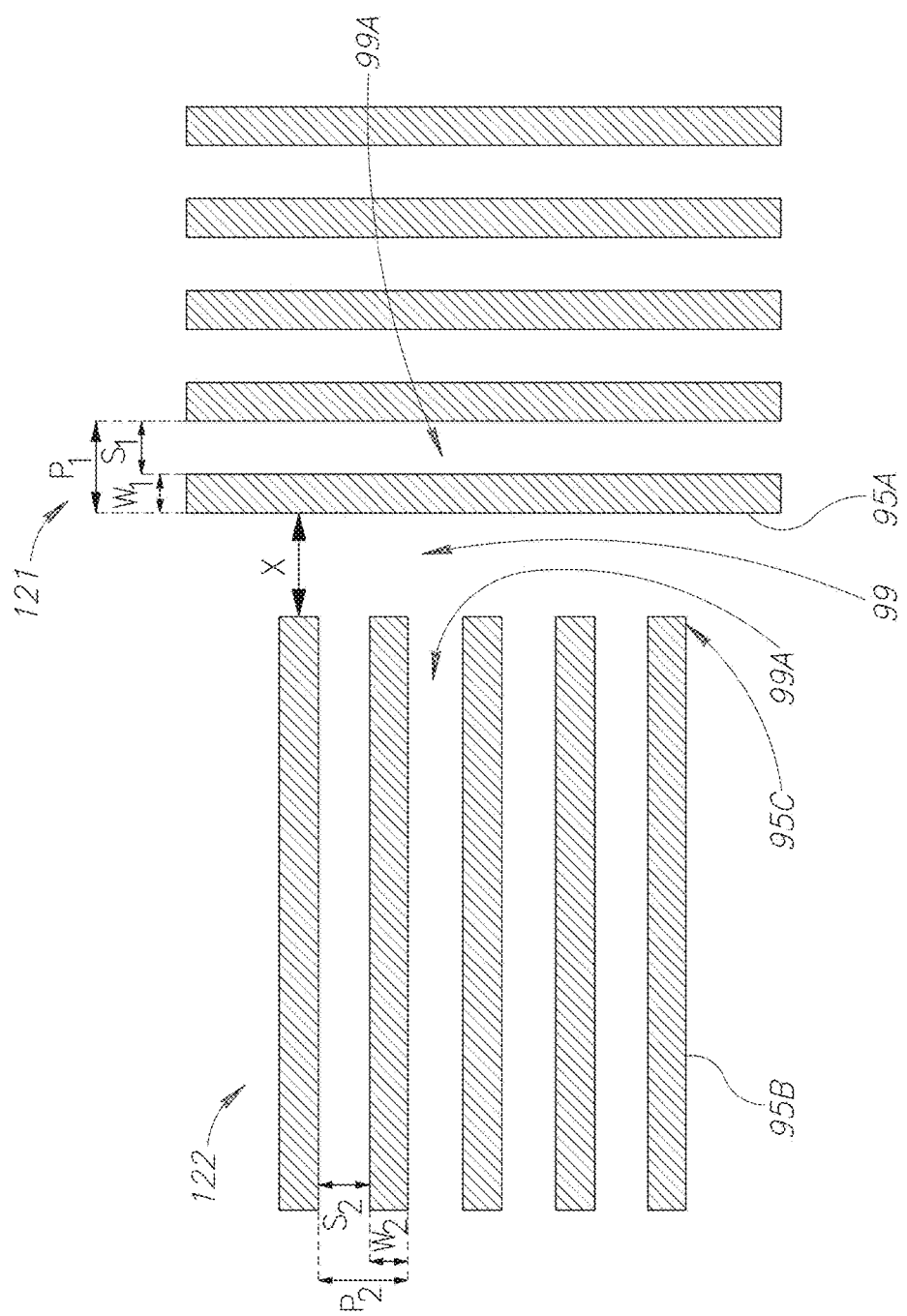
FIG. 8 is a high level schematic illustration of a border region between target structures of a metrology target, according to some embodiments of the invention.

FIG. 8 is a high level schematic illustration of a border region 99 between target structures 121, 122 of metrology target 140, according to some embodiments of the invention. Target structures 121, 122 may be target elements and background structures (i.e., numerals 121, 122 may be switched), different target elements or any other features of target 140. Target structures may be guidelines 95 for a DSA process. Target structures 121, 122 are characterized by structure widths $W_1$, $W_2$; gap widths $S_1$, $S_2$ between structures and structure pitches $P_1$, $P_2$, respectively. A characteristic width of border region 99 generally comprises a designed width and an inaccuracy factor which may increase or decrease the actually produced border region width X.

The non-limiting example illustrated in FIG. 8 schematically presents some of the details of metrology target 140 comprising at least two adjacent target structures 121, 122 produced by a directed self-assembly (DSA) process, wherein border region 99 between target structures 121, 122 comprises a first guiding line 95A of one of the target structures (in the illustrated case—target structure 121) and a plurality of guiding line ends 95C of respective guidelines 95B of the other target structure (in the illustrated case—target structure 122).

It is noted that the term "target structure" is used in the present disclosure to refer to a part of a target, such as a target feature or a background feature. Target structures may be bar-like or area-like, e.g. in case of target features in AIM and AIMid target respectively, or be frame-like, enclosing other target structures, e.g., in case of the peripheral background of such targets. The term "target element" is used in the present disclosure to refer to a continuous element in a target structure, such as a segment or an unsegmented bar which is set within a background.

Guiding line ends 95C at border region 99 are designed to maintain a distance below a specified threshold to first guiding line 95A, upon producing targets 140 with a width of the border region being up to a specified maximal process inaccuracy threshold associated with a respective guideline production process. That is, actually produced border region width X may be larger or smaller than the designed border width due to inaccuracy factors. The specified threshold may be selected to yield parallel self-assembly of polymer molecules in the DSA process. The specified threshold may be defined with respect to a range of possible actual border regions widths, taking into account the process inaccuracies.

Without being bound by theory, actual width X of border region 99 influences the DSA process, and in particular it influences the level of order of polymer molecules 98A, 98B as they polymerize in border region 99. It is noted that while guidelines 95 may be configured to ensure ordered polymerization therebetween, the border region may be characterized by less uniform features (in the example illustrated in FIG. 8, guiding lines 95B which are perpendicular to guiding line 95A), and higher sensitivity to process inaccuracy (in the example illustrated in FIG. 8, the inaccuracy in the spacing between target structures 121, 122 may be greater than the inaccuracy in the spacing between guiding lines 95B), and thus polymerization in border regions may be less regular and the level of order in border region 99 may be more sensitive to process inaccuracies. As metrology in general, and specifically overlay metrology, is very sensitive to the border regions, the following targets and methods are particularly advantageous for these purposes.

Figure 9A:
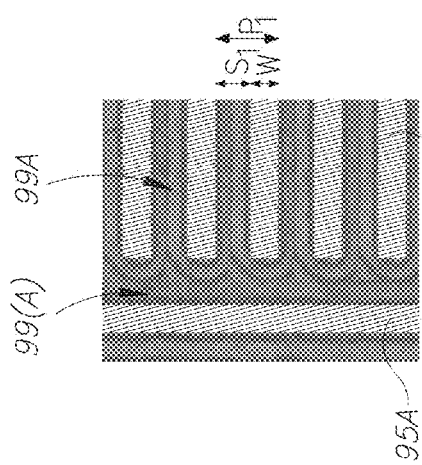
FIG. 9A is a high level schematic illustration of border regions between target structures and resulting levels of order in polymer surfaces produced using a DSA process, according to some embodiments of the invention.
Figure 9C:
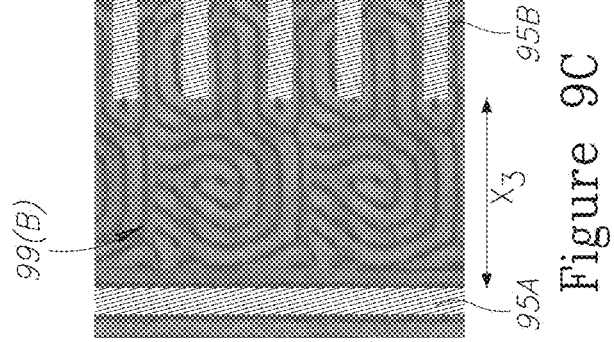
FIG. 9C is a high level schematic illustration of border regions between target structures and resulting levels of order in polymer surfaces produced using a DSA process, according to some embodiments of the invention.
Figure 9B:
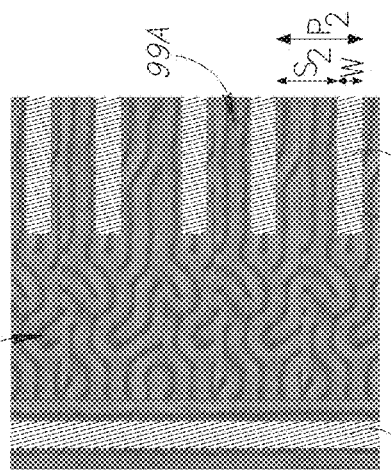
FIG. 9B is a high level schematic illustration of border regions between target structures and resulting levels of order in polymer surfaces produced using a DSA process, according to some embodiments of the invention.

FIGS. 9A-9C are high level schematic illustrations of border regions 99 between target structures 121, 122 and resulting levels of order in polymer surfaces produced using a DSA process, according to some embodiments of the invention. The illustrations are qualitative, as the images of polymer lines 98A, 98B are schematic and do not necessarily represent the exact details of formed lines, but should be understood as merely illustrating the level of order in the border regions that results from the respective target designs.

Specifically, as width X of border region 99 increases from $X_1$ in FIG. 9A through $X_2$ in FIG. 9B to $X_3$ in FIG. 9C, the level of order decreases from ordered polymer lines 99(A) through an intermediate level of disorder 99 (intermediate) to disordered polymer lines 99(B). The level of order is not necessarily monotonous with the spacing X, as there may be local values of X exhibiting a local maximum (or a local minimum) of the level of order, related to the ratio between X and the DSA pitch. X values corresponding to local maxima in the level of order may be selected for the target design. It is noted that FIGS. 9A-9C schematically illustrate a similar sequence of decreasing order level between guiding lines 95B with increasing spaces therebetween, namely with the increasing size of the spaces from $S_1$ through $S_2$ to $S_3$ (and parallel increase of the pitches of guiding lines 95B from $P_1$ through $P_2$ to $P_3$) respectively, the ordered polymer lines between guiding lines 95B become unordered when the spaces $S_3$ become large and border regions 99 become disordered (FIG. 9C). It is noted that as polymer lines 98 are generally continuous, the level of order in border region 99 influences the level of order between guiding line ends 99C and vice versa. The inventors have found that achieving ordered border regions 99(A) is a significant challenge, especially in face of production inaccuracies, and that disordered border regions 99(B) introduce errors that may become detrimental to the metrological measurements, as disordered regions 99(B) are periodical and hence their optical effects may under certain circumstances add up and influence the metrology results substantially.

Figure 10B:
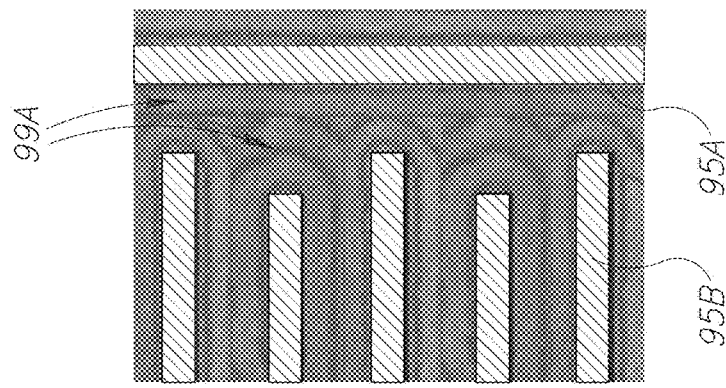
FIG. 10B is a high level schematic illustration of a target element design with guiding lines of alternating lengths and resulting levels of order in polymer surfaces in the border regions between target structures, respectively, according to some embodiments of the invention.
Figure 10A:
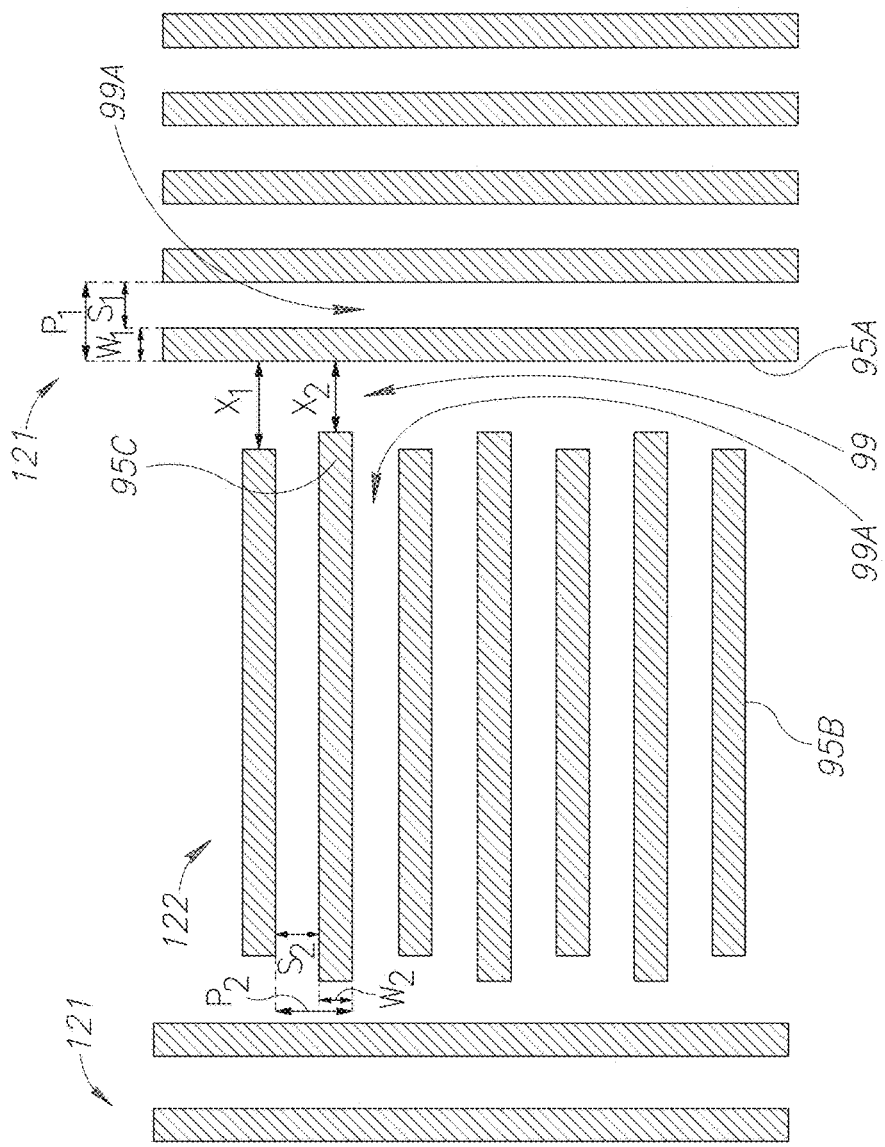
FIG. 10A is a high level schematic illustration of a target element design with guiding lines of alternating lengths and resulting levels of order in polymer surfaces in the border regions between target structures, respectively, according to some embodiments of the invention.
Figure 11B:
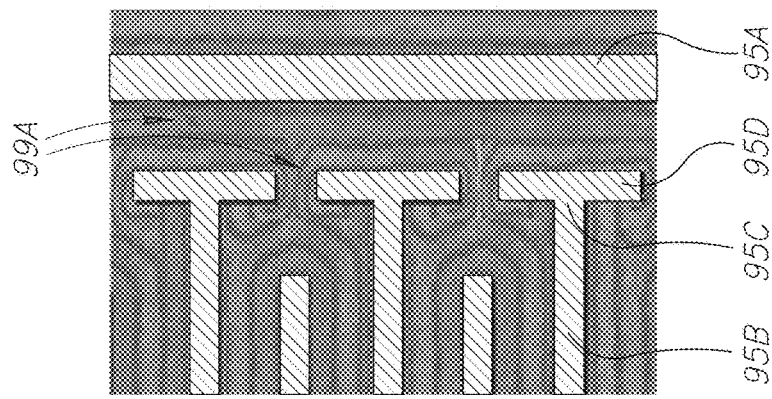
FIG. 11B is a high level schematic illustration of a target element design with ends parallel to the adjacent target element and resulting levels of order in polymer surfaces in the border regions between target structures, respectively, according to some embodiments of the invention.
Figure 11A:
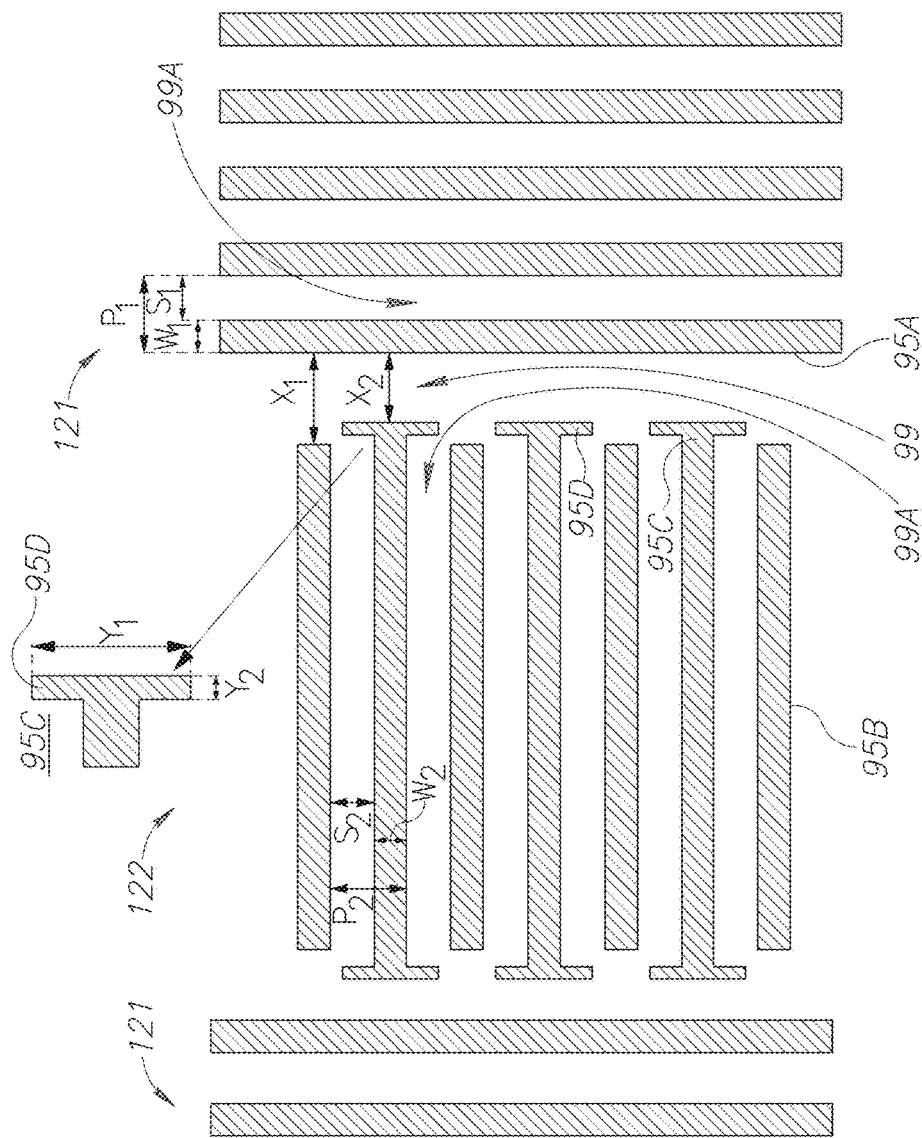
FIG. 11A is a high level schematic illustration of a target element design with ends parallel to the adjacent target element and resulting levels of order in polymer surfaces in the border regions between target structures, respectively, according to some embodiments of the invention.
Figures 12A, 12B:
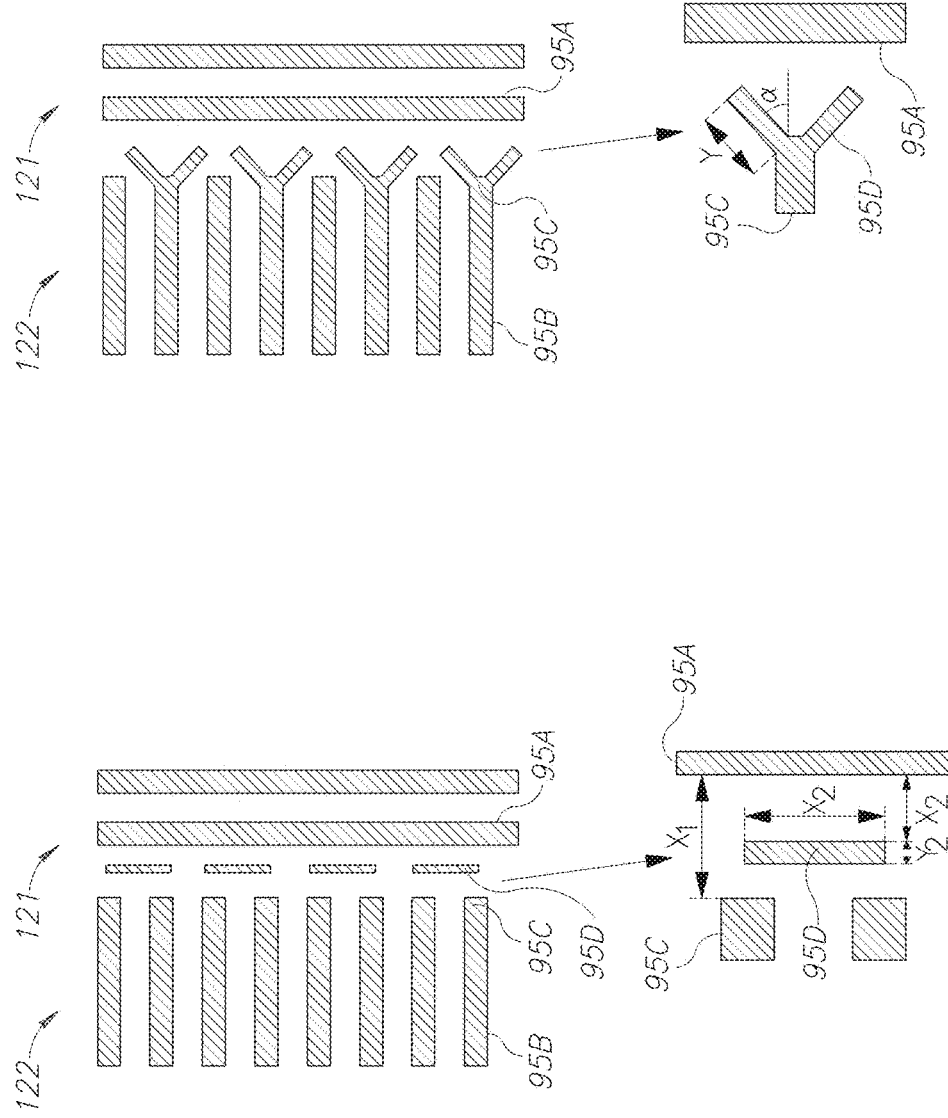
FIG. 12A is a high level schematic illustration of two further target element designs, according to some embodiments of the invention.
FIG. 12B is a high level schematic illustration of two further target element designs, according to some embodiments of the invention.

FIGS. 10A and 10B are high level schematic illustrations of a target element design with guiding lines 95B of alternating lengths and resulting levels of order in polymer surfaces in border regions 99 between target structures 121, 122, respectively, according to some embodiments of the invention. FIGS. 11A and 11B are high level schematic illustrations of a target element design with ends 95C parallel to the adjacent target element (i.e., guideline 95A) and resulting levels of order in polymer surfaces in border regions 99 between target structures 121, 122, respectively, according to some embodiments of the invention. FIGS. 12A and 12B are high level schematic illustrations of two further target element designs, according to some embodiments of the invention.

FIG. 10-12 schematically illustrate a range of solutions that allow controlling, at least to some extent, the level of order of polymer lines 98 within border region 99 in face of given production inaccuracies. These solutions and non-limiting and exemplary, and similar solutions, which are likewise part of the present invention, may be constructed according to the disclosed principles.

For example, FIGS. 10A and 10B schematically illustrate guiding lines 95B having varying and alternating lengths which function to narrow border region 99 and hence limit the ability of polymer lines to spread after exiting the spaces between guidelines 95. In the illustrated example, the actual width of border region 99 is defined by two parameters, $X_1$ and $X_2$, which result from the design and the production inaccuracies. Guiding line ends 95C may be designed to protrude beyond other guiding line ends 95C with respect to first guiding line 95A. In particular, protruding guideline ends 95C of longer guidelines 95B fill in some of border region 99 and direct polymerization into a more ordered pattern than the one shown, e.g., in FIG. 9C with guiding line ends 95C having same distance $X_3$ from adjacent guiding line 95A. Similar designs may comprise any form and pattern of protruding guideline ends 95C into border region 99. For example, several distances to guideline 95A may be selected, different proportions of elongated guidelines 95B may be selected and different relations between neighboring border regions 99 may be designed.

Guiding line ends 95C may be designed to have end-sections 95D which are parallel to first guiding line 95A. For example, FIGS. 11A and 11B schematically illustrate hammer-headed guideline ends 95C, having end-sections 95D parallel to first guiding line 95A. In such design, border regions 99 are split into smaller sub-regions between end-sections 95D and guideline ends 95C, which may be unordered (but small) or ordered similarly or differently from their surroundings; and larger sub-regions between end-sections 95D and guiding line 95A, which may be highly ordered regions 99A (exhibiting, e.g., parallel-line patterns). Either or both parts may exhibit repeatable patterns which may be accounted for by the measurement algorithms and/or by the measuring optics. Without being bound by theory, border regions 99 may be ordered due to the parallel orientation of end-sections 95D and guiding line 95A and the resulting smaller sensitivity of the level of order in this region to process inaccuracies. End sections 95D may be designed to force a different order in border regions 99 than the order between lines 95. The forced order may be repeatable to allow the metrology measurement to be stable and repeatable, across targets and process conditions.

FIG. 12A schematically illustrates end-sections 95D which are parallel to guiding line 95A and detached from guidelines 95B. The dimensions ($Y_1$, $Y_2$), positions and spacing ($X_1$, $X_2$, etc.) between end-sections 95D may be selected to maximize the level of order in border region 99. FIG. 12B schematically illustrates end-sections 95D attached to some of guideline ends 95C and formed to improve polymerization order in border region 99. For example, slanted end-sections 95D (having width Y and angle α) may be designed to direct polymerization in an ordered manner and reduce a size of the potentially unordered regions or even better, eliminate them. Furthermore, guideline ends 95C and/or end-sections 95D may be designed to yield polymerization patterns in border regions 99 that do not reduce the accuracy of metrology measurements without necessarily forcing ordered polymerization in border regions 99. For example, in cases where polymerization in a border region is disordered but random, i.e., different patterns occur at different areas of border region 99, the optical effect of border regions 99 may not accumulate and hence not reduce the metrology accuracy. Hence, guideline ends 95C and/or end-sections 95D may to some extent be designed to vary within each border region 99 in a way that reduces the measurement inaccuracy. Alternatively, guideline ends 95C and/or end-sections 95D may be designed to produce a measurement error which is removable algorithmically.

A method 300 may comprise producing two adjacent target structures or target elements by a directed self-assembly (DSA) process, wherein a border region between the target structures comprises a first guiding line of one of the target structures and a plurality of guiding line ends of respective guidelines of the other target structure. Method 200 may comprise designing the guiding line ends at the border region to maintain a distance below a specified threshold to the first guiding line, upon producing the target elements with a width of the border region being up to a specified maximal process inaccuracy threshold associated with a respective guideline production process. Method 300 may further comprise any of selecting the specified threshold to yield parallel self-assembly in the DSA process: designing the guiding line ends to have end-sections which are parallel to the first guiding line; and designing the guiding line ends to protrude beyond other guiding line ends with respect to the first guiding line. Method 300 may be applied to adjacent target element pairs in designing metrology targets. Provided is a computer program product comprising a computer readable storage medium having computer readable program embodied therewith. The computer readable program is configured to carry out the method of designing and optimizing metrology targets which uses method 300. Also provided is a computer program product comprising a computer readable storage medium having computer readable program embodied therewith. The computer readable program is configured to carry out metrology measurements of the produced targets. See further stages of method 300 in FIG. 27 below. The disclosed design and production elements and steps regarding the border regions between target structures may be incorporated to design and production of any of the designs of metrology targets 140 that are illustrated below.

FIG. 13-17 are high level schematic illustrations of several AIM target DSA designs, according to some embodiments of the invention. Metrology targets 140 comprise at least one layer (previous layer 130 and/or current layer 135, see FIGS. 4B and 5-7, or any intermediate layer in multi-layered targets) produced by a directed self-assembly (DSA) process. In the respective layer, at least one target element and/or target structure is distinguished from its respective background by at least one characteristic of the DSA process. It is noted that the term "target structure" is used to refer to a part of target 140, such as a target feature or a background feature, while the term "target element" is used in the present disclosure to refer to a continuous element in a target structure, such as a segment or an unsegmented bar or area which is set within a background. Specifically, segmenting target structures may improve their production accuracy and/or enhance metrology performance by removing inaccuracies and enhancing the measurement signals and improving the distinction between target structures. It is further noted, that the lines illustrated in FIGS. 13-17 may be understood as denoting guiding lines 95 for the DSA process or as denoting polymer lines 98 produced by the DSA process. In particular, the specific widths and spatial frequencies of the lines serves illustrative purposes only, and may vary in actual designs with respect to practical consideration and the identification of the lines as guiding lines 95 or polymer lines 98. In either case, enhancement of ordered regions of polymer lines may be carried out as a production step of the target, as disclosed above. Measuring technology (optics, algorithms) may be adapted to the specific character of lines 95, 98 and post processing. While FIG. 13-17 illustrate the design and production principles using AIM targets, the scope of the present invention clearly comprises any type of target 140 (e.g., SCOL, AIMID, BLOSSOM, BiB) made of any type of target structures and target elements, which are designed according to the disclosed principles. Specifically, hard masks, rod-like molecules and border region design may be applied to any of the DSA-produced, segmented targets 140.

The characteristic of the DSA process used to distinguish target elements or structures from their respective background may be a presence and/or a direction and/or a spatial frequency and/or length and width of DSA guiding lines. In certain embodiments, at least one characteristic of the DSA process may be configured to enable distinction between target element(s) and its background using polarized light.

Figure 13:
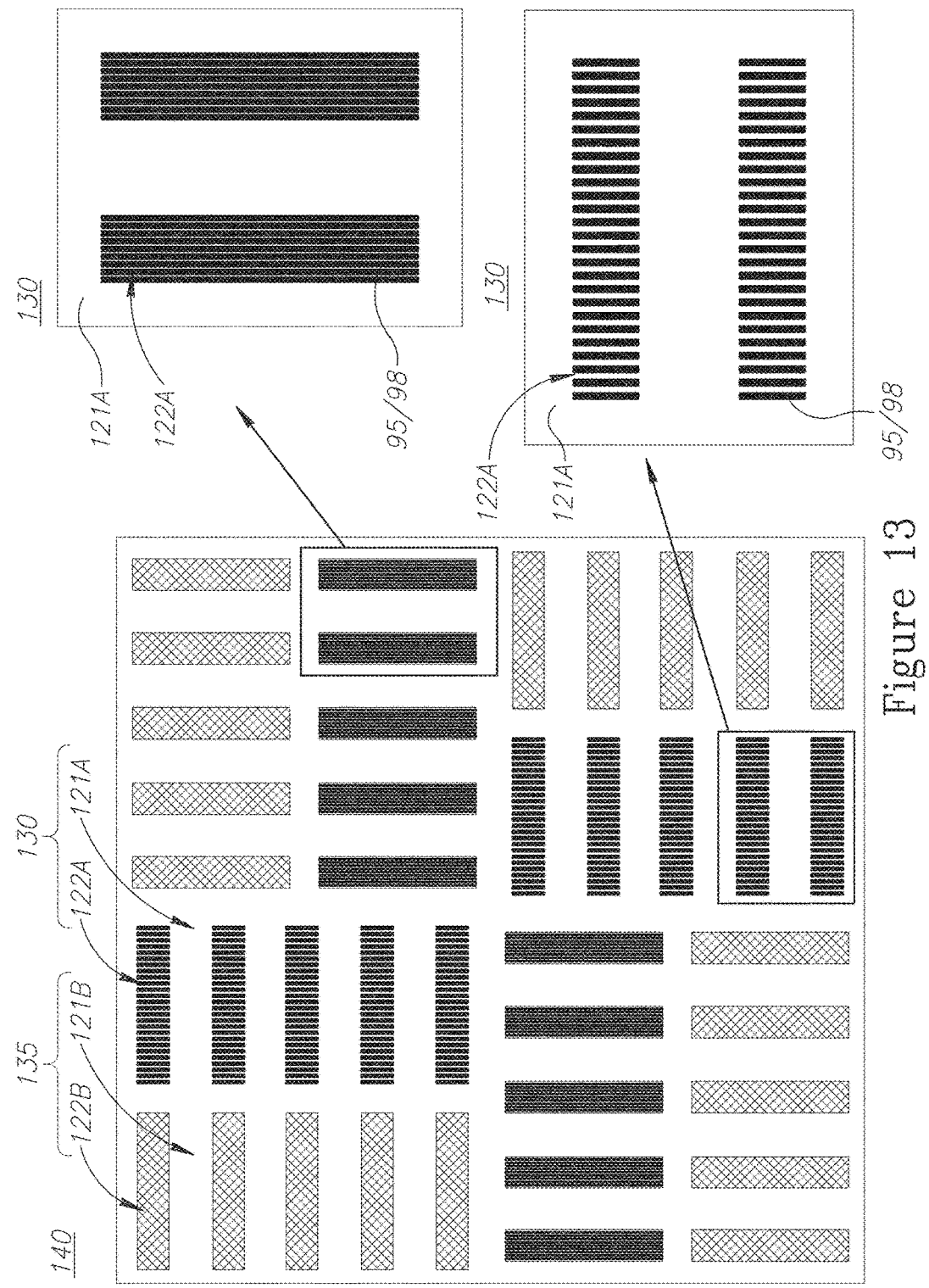
FIG. 13 is a high level schematic illustration of several AIM target DSA designs, according to some embodiments of the invention.

For example, FIG. 13 schematically illustrates AIM target 140 having unsegmented background 121A, 121B in both layers 130, 135 respectively, unsegmented target structures 122B in current layer 135 and segmented target elements 122A in previous layer 130. In certain embodiments, any of backgrounds 121A, 121B and target structures 122B may be segmented, e.g., perpendicularly to target elements 122A. The segmentation may vary throughout target 140, e.g., in FIG. 13 a segmenting spatial frequency, implementable by designing respective guiding lines 95 for the DSA process, differs between the target structures for two perpendicular directions (X and Y) while the segmentation direction is similar. Clearly, segmentation direction may also vary among target structures and among target elements.

Figure 14:
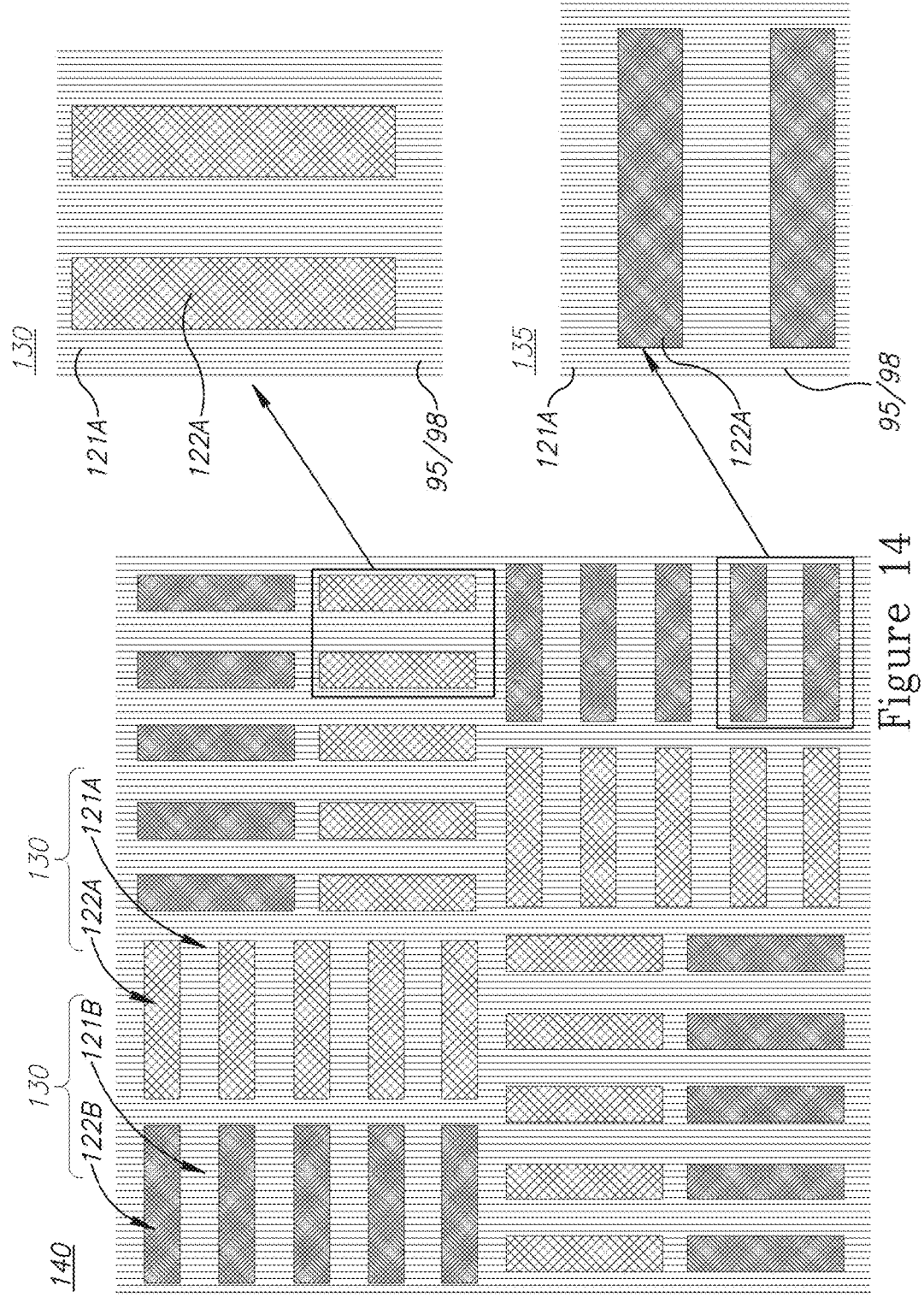
FIG. 14 is a high level schematic illustration of several AIM target DSA designs, according to some embodiments of the invention.

In another example, FIG. 14 schematically illustrates AIM target 140 having segmented background 121A, 121B in both layers 130, 135 respectively, and unsegmented target structures 122A, 122B in previous layer 130 and current layer 135 respectively. In certain embodiments, any of target structures 122A, 122B may be segmented, e.g., perpendicularly to background 121A, 121B. The segmentation may vary throughout target 140 in any of its characteristics.

Figure 15:
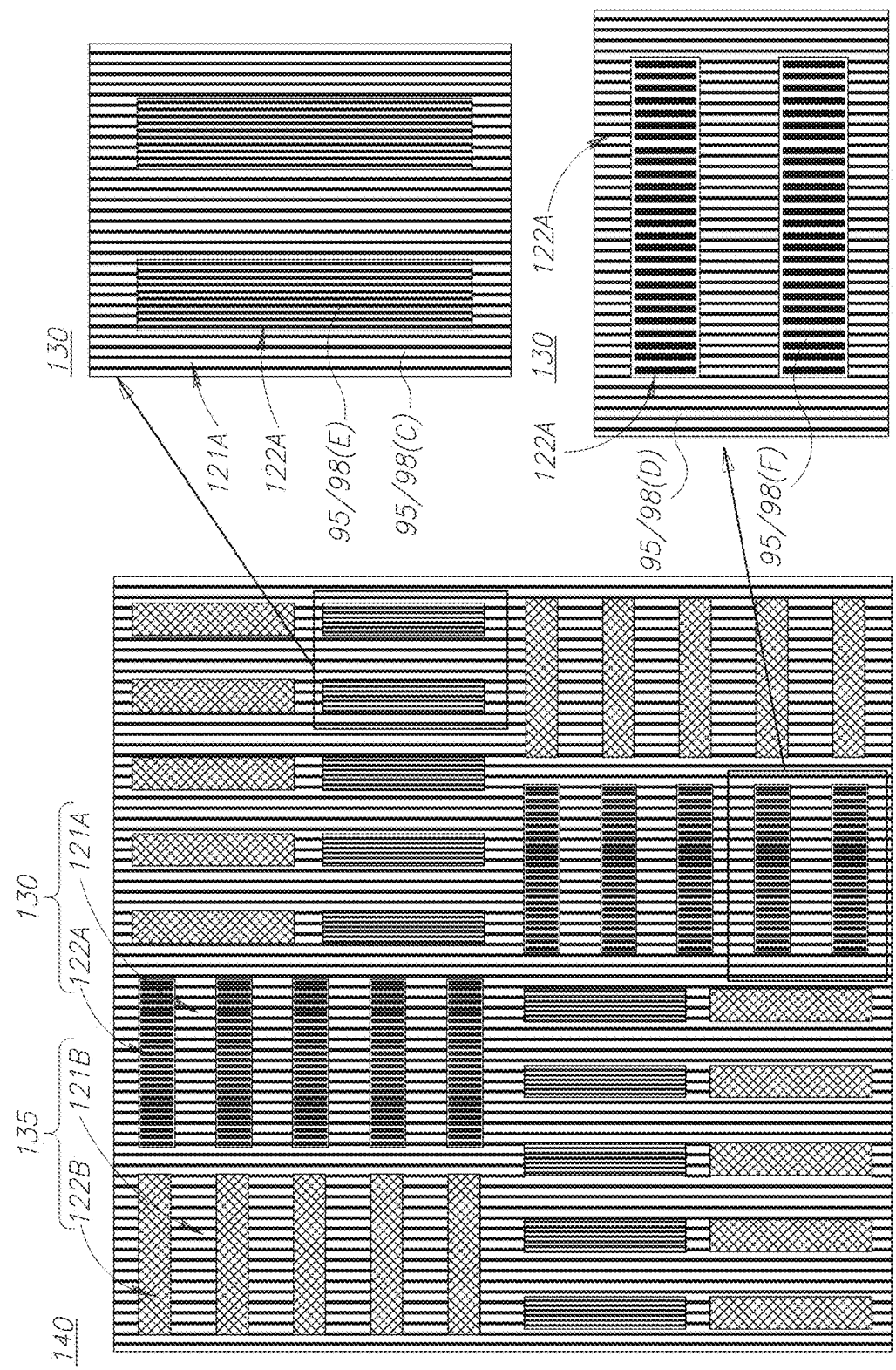
FIG. 15 is a high level schematic illustration of several AIM target DSA designs, according to some embodiments of the invention.

In another example, FIG. 15 schematically illustrates AIM target 140 having segmented background 121A, 121B in both layers 130, 135 respectively, unsegmented target structures 122B in current layer 135 and segmented target elements 122A in previous layer 130. In certain embodiments, target structures 122B may be segmented, e.g., perpendicularly to background 121A, 121B (and/or to segmented target elements 122A in certain examples). The segmentation may vary throughout target 140, e.g., in FIG. 15 a segmenting spatial frequency and line width, implementable by designing respective guiding lines 95 for the DSA process, differ between the target structures for two perpendicular directions (X and Y) while the segmentation direction is similar. Clearly, segmentation direction may also vary among target structures and among target elements.

Figure 16:
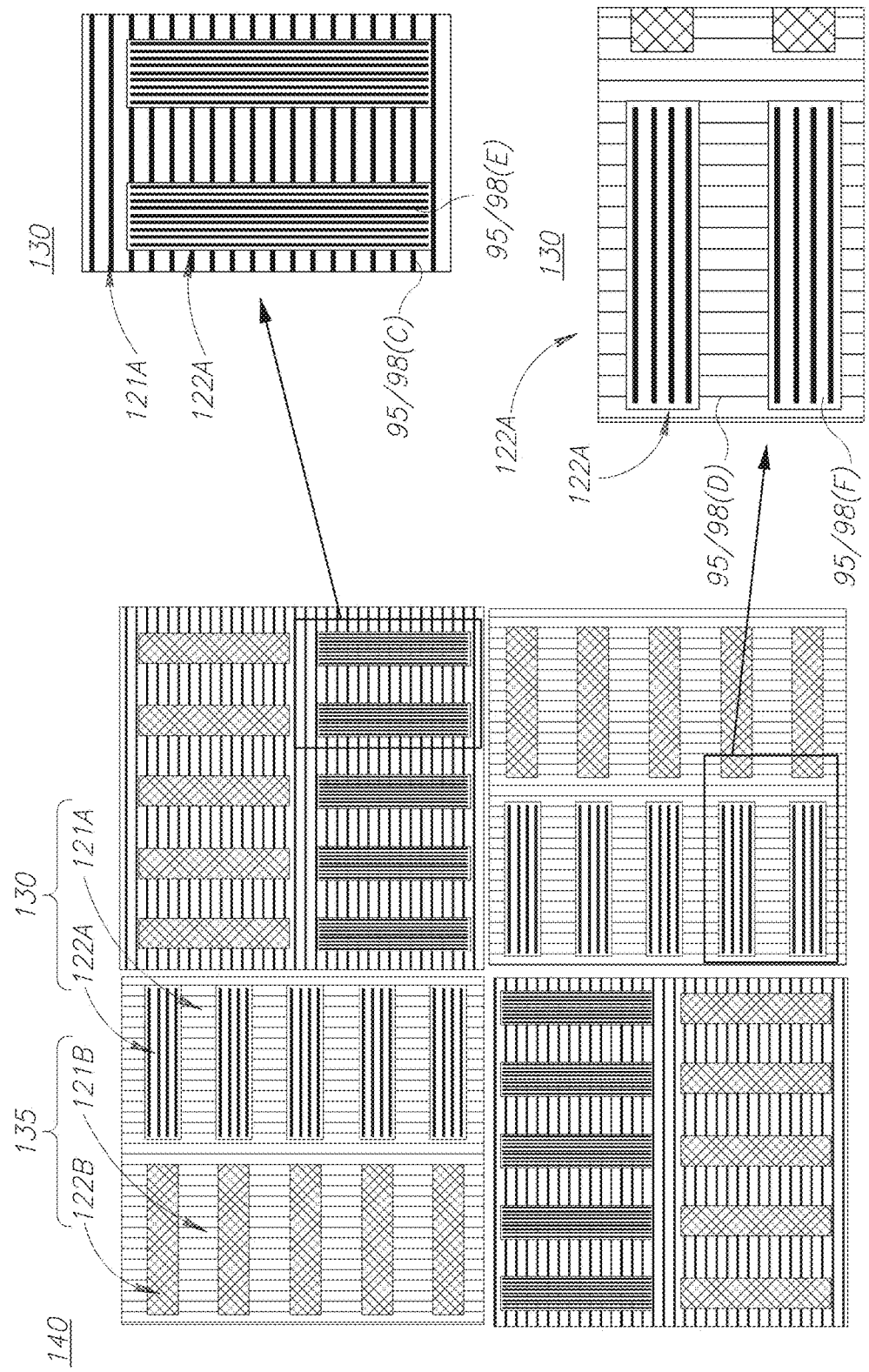
FIG. 16 is a high level schematic illustration of several AIM target DSA designs, according to some embodiments of the invention.

In still another example, FIG. 16 schematically illustrates AIM target 140 having segmented background 121A, 121B in both layers 130, 135 respectively, unsegmented target structures 122B in current layer 135 and segmented target elements 122A in previous layer 130. In certain embodiments, target structures 122B may be segmented, e.g., perpendicularly to background 121A, 121B (and/or to segmented target elements 122A in certain examples). The segmentation may vary throughout target 140, e.g., in FIG. 16 a segmenting spatial frequency, line direction and line width, implementable by designing respective guiding lines 95 for the DSA process, vary among the target structures and backgrounds. Specifically, the following guiding/polymer lines (95/98 respectively) may vary among target structures: lines 95/98(C) in background 121 of X-direction structures, lines 95/98(D) in background 121 of Y-direction structures, lines 95/98(E) in target structure 122 of X-direction structures, and lines 95/98(F) in target structure 122 of Y-direction structures. These and other subgroups of lines may differ in any of a presence, a direction, a spatial frequency, a dimension of DSA guiding lines 95 and/or resulting polymer lines 98. Clearly, target structures 122B in current layer 135 may also be segmented, and backgrounds 121A, 121B in previous and current layers 130, 135 respectively may have different segmentation, differing in at least one characteristic of the DSA process.

Figure 17:
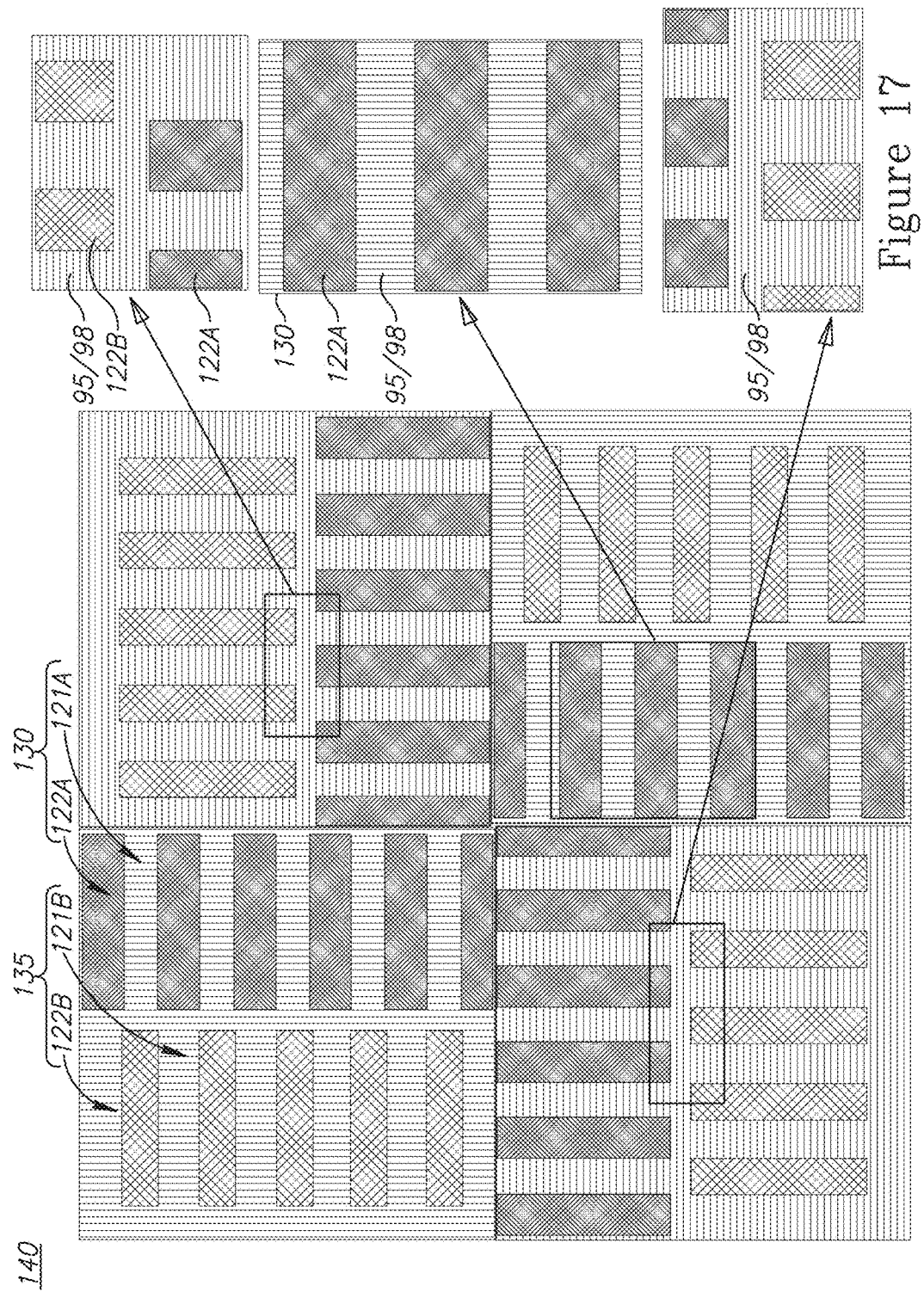
FIG. 17 is a high level schematic illustration of several AIM target DSA designs, according to some embodiments of the invention.

In another example, FIG. 17 schematically illustrates AIM target 140 having segmented background 121A, 121B in both layers 130, 135 respectively, and unsegmented target structures 122A, 122B in previous layer 130 and current layer 135 respectively. In certain embodiments, any target structures 122A, 122B may be segmented, e.g., perpendicularly to background 121A, 121B. The segmentation may vary throughout target 140 in any of its characteristics. For example, as illustrated in FIG. 17, background segmentation varies between different quadrants of target 140. Additionally, as target structures 122A, 122B are not aligned, guiding lines 95 for the DSA process may be adapted to yield ordered border regions (see e.g., top and bottom magnified areas) between structures and between elements, as disclosed above. As is also seen in FIG. 17, target element sizes may vary between different target structures and the segmentation may be varied accordingly.

Figure 18:
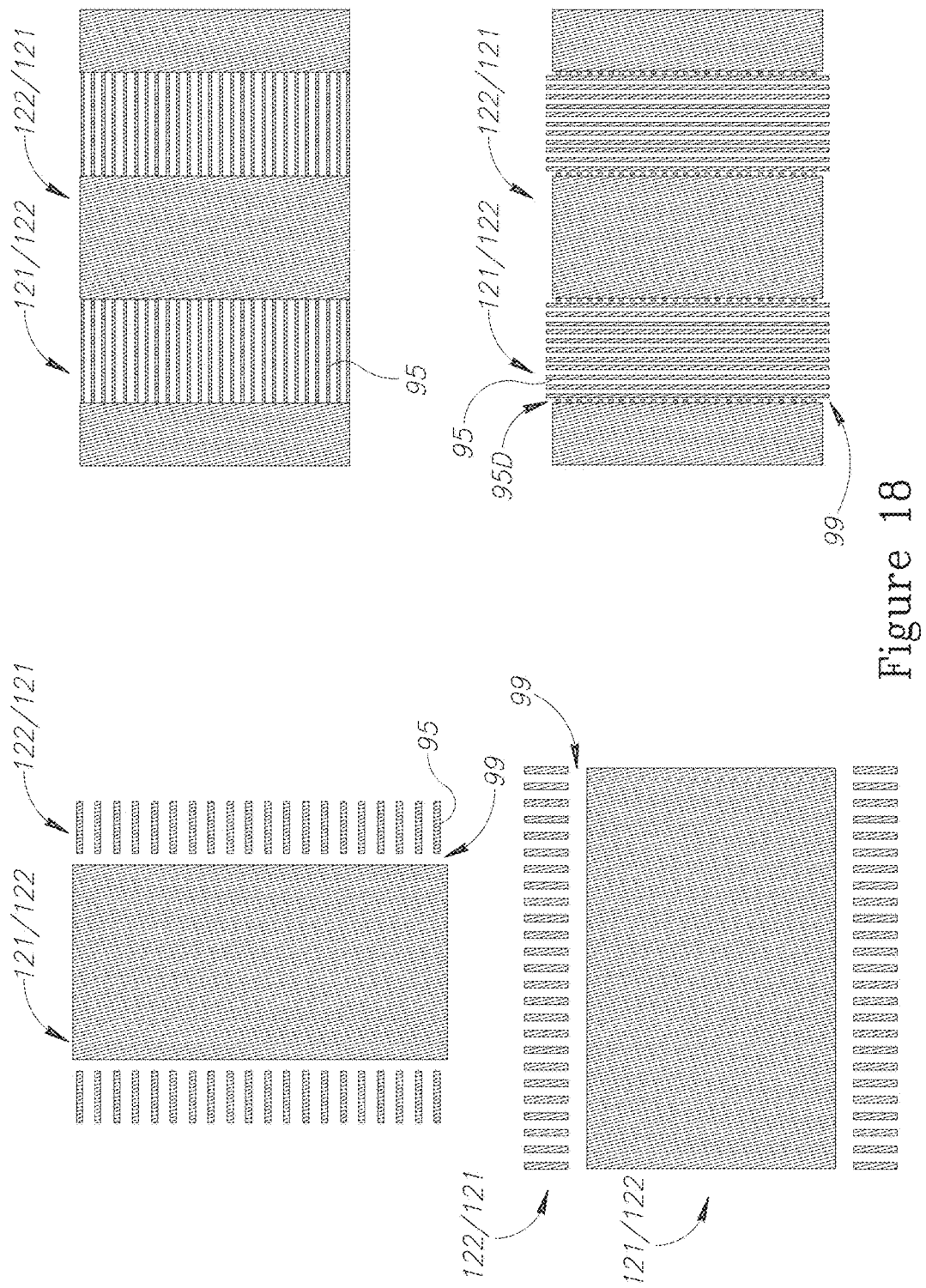
FIG. 18 is a high level schematic illustration of several types of border regions in target designs, exemplified on an AIM target DSA design, according to some embodiments of the invention.

FIG. 18 is a high level schematic illustration of several types of border regions in target designs, exemplified on an AIM target DSA design, according to some embodiments of the invention. Exact target designs may implement the border region design principles disclosed above (e.g., in FIGS. 8-12) to any of the border regions in the designs, to control the level of order in the produced DSA polymer surface. Moreover, additional processing may be applied to order and to unordered regions to produce or use the targets, as disclosed above (e.g., in FIG. 1-3). FIG. 18 schematically illustrates various types of border regions 99 between target structures 121, 122 (any of the illustrated structures may be considered either target element or background, with the adjacent structure being background or target elements, respectively). Border region 99 may be between guiding lines 95 and a solid target element (left), may be missing if guiding lines 95 continue a solid target element (top right) or may comprise end-segments 95D filling up border region 99 (bottom right), e.g., to compensate for possible inaccuracies, as explained above.

Figure 19:
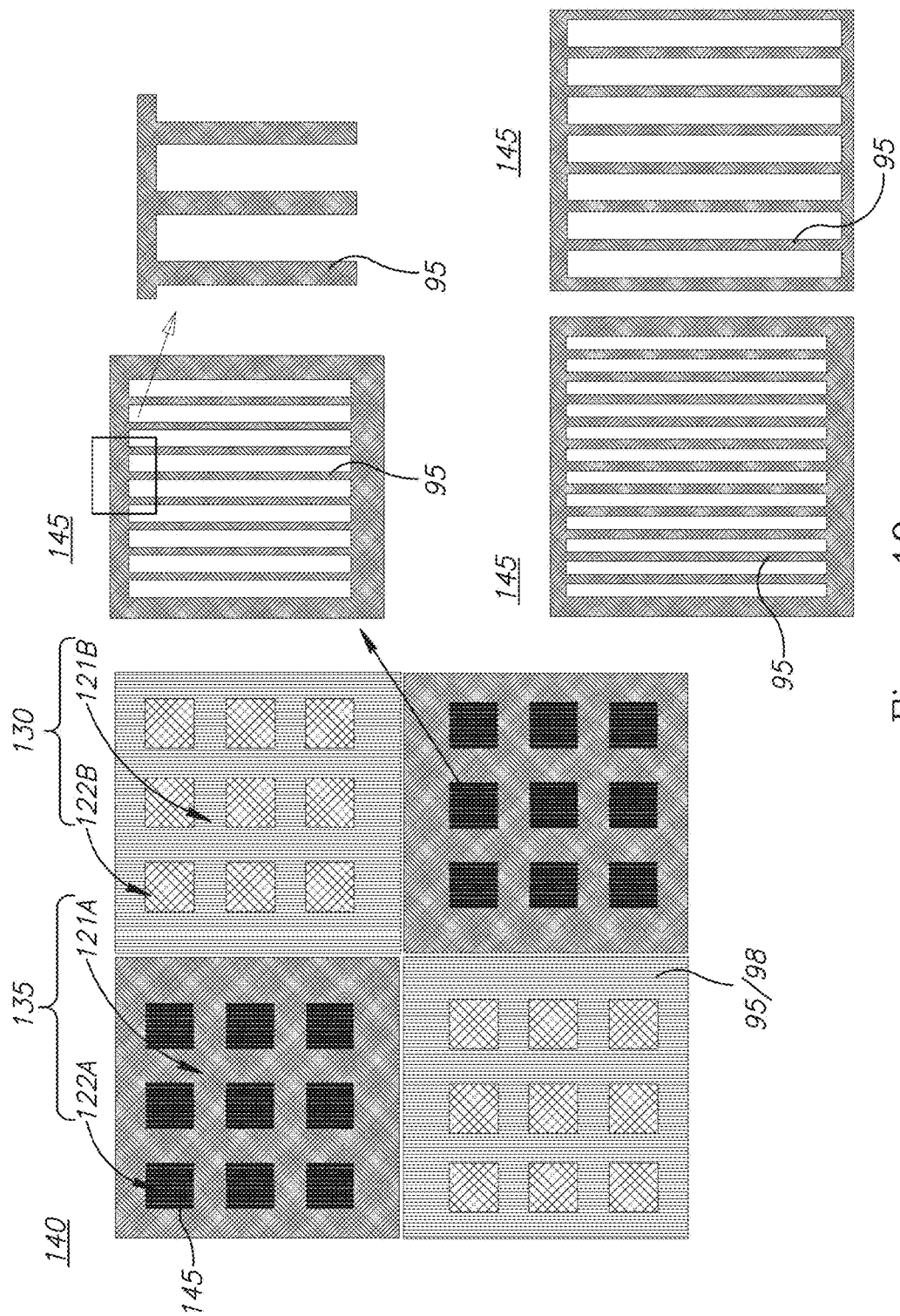
FIG. 19 is a high level schematic illustration of several AIMid target DSA designs, according to some embodiments of the invention.
Figure 21:
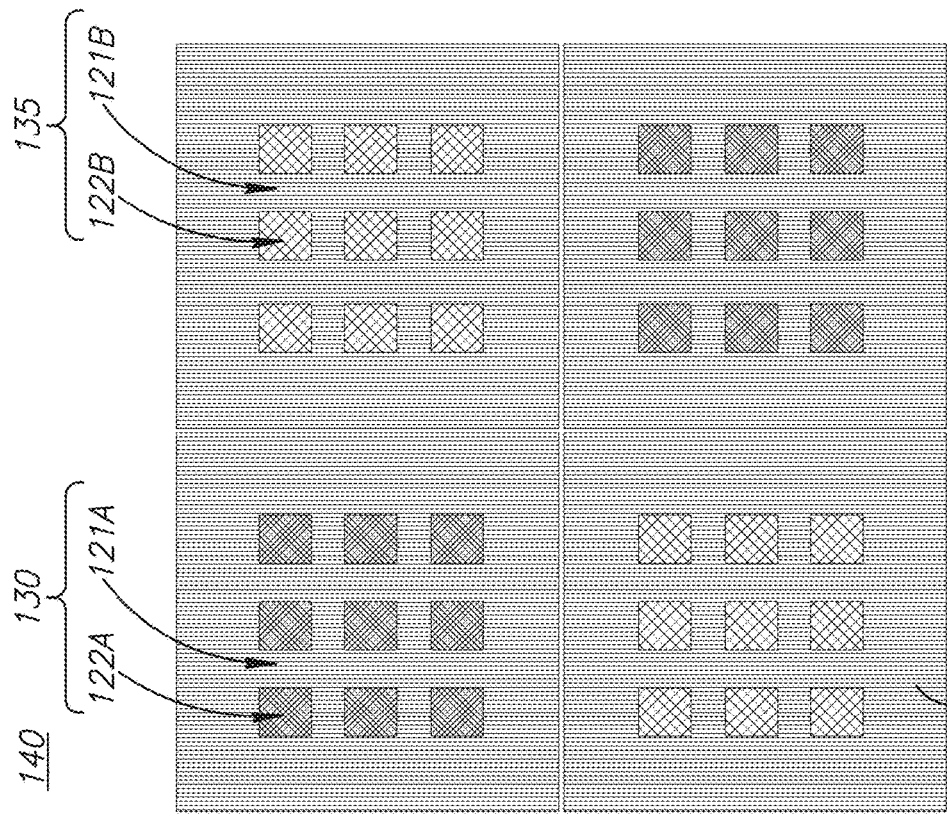
FIG. 21 is a high level schematic illustration of several AIMid target DSA designs, according to some embodiments of the invention.
Figure 20:
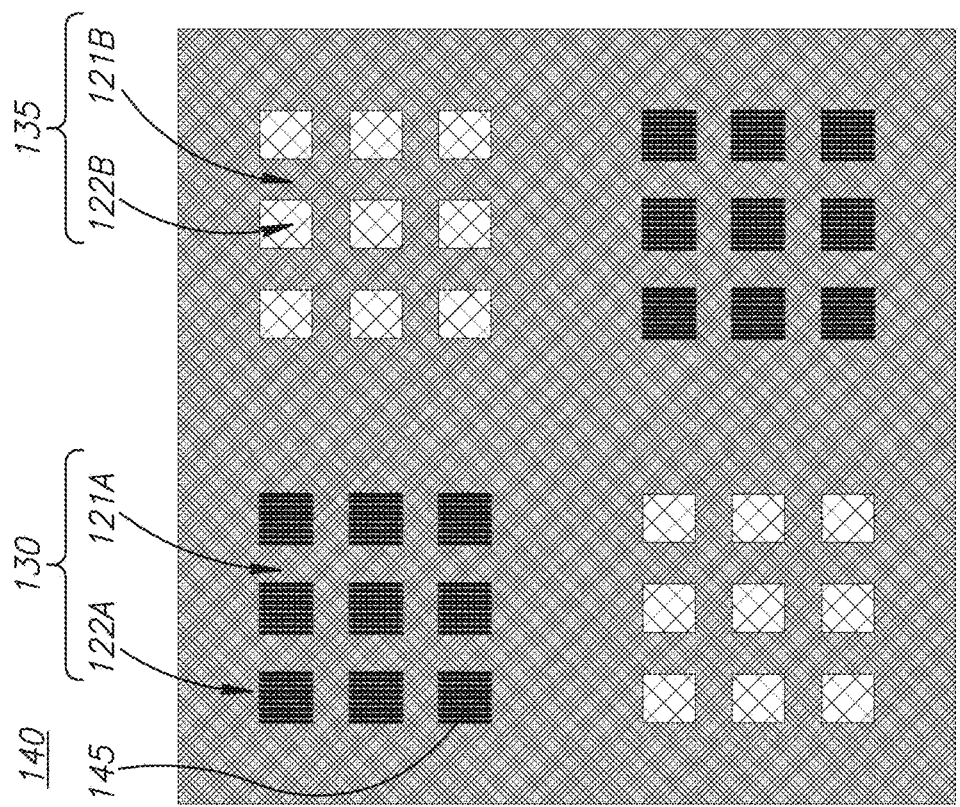
FIG. 20 is a high level schematic illustration of several AIMid target DSA designs, according to some embodiments of the invention.

FIG. 19-21 are high level schematic illustrations of several AIMid target DSA designs, according to some embodiments of the invention. FIG. 19 further schematically illustrates several types of border regions in target designs, exemplified on the AIMid target DSA designs, according to some embodiments of the invention.

FIG. 19-21 schematically illustrate design varieties of segmented AIMid targets 140, which represent some of the segmentation possibilities. For example, FIG. 19 schematically illustrates segmented target structures 122A on unsegmented background 121A in previous layer 130 and unsegmented target structures 122B on segmented background 121B in previous layer 135. In certain embodiments, background 121A and/or target structures 122B may be segmented, e.g., perpendicularly to background 121B and/or to segmented target elements 122B, depending on specific target configuration features. Clearly, reversing the design between previous and current layers 130, 135 respectively, adapting the design for producing multilayered targets and any combination of segmentations of the target structures and respective backgrounds are likewise within the scope of the present invention. FIG. 19 further illustrates various embodiments of a single target structure 145 which may be designed differently with respect to target size and requirements for the DSA process. Guiding lines 95 may be designed to mean specific dimensional criteria relating to target size and DSA process requirements from generating ordered polymer lines. FIG. 20 schematically illustrates targets 140 with one set of target structures 122A segmented over unsegmented (or segmented perpendicularly) background 121A and another unsegmented set of target structures 122B segmented over unsegmented (or segmented perpendicularly) background 121B. FIG. 21 schematically illustrates targets 140 with unsegmented (or segmented perpendicularly) target structures 122A, 122B segmented over segmented background 121A, 121B. The segmentation may vary throughout target 140, e.g., with respect to the segmenting spatial frequency, the direction of segmentation, the dimension (width, length) of the segments, and the spacing between segments, which is implementable by designing respective guiding lines 95 for the DSA process.

Figure 22:
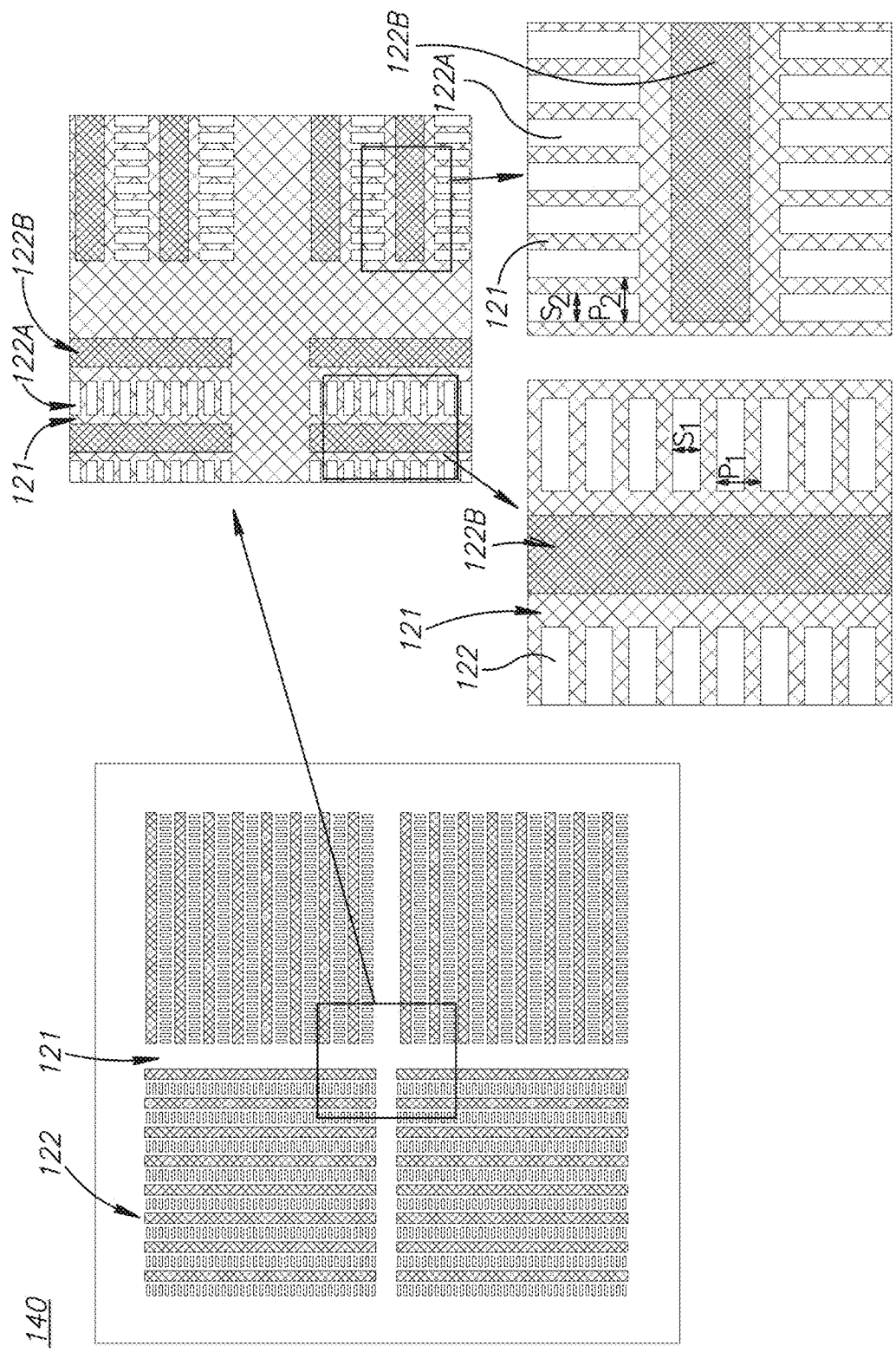
FIG. 22 is a high level schematic illustration of several SCOL target DSA designs, according to some embodiments of the invention.
Figure 23:
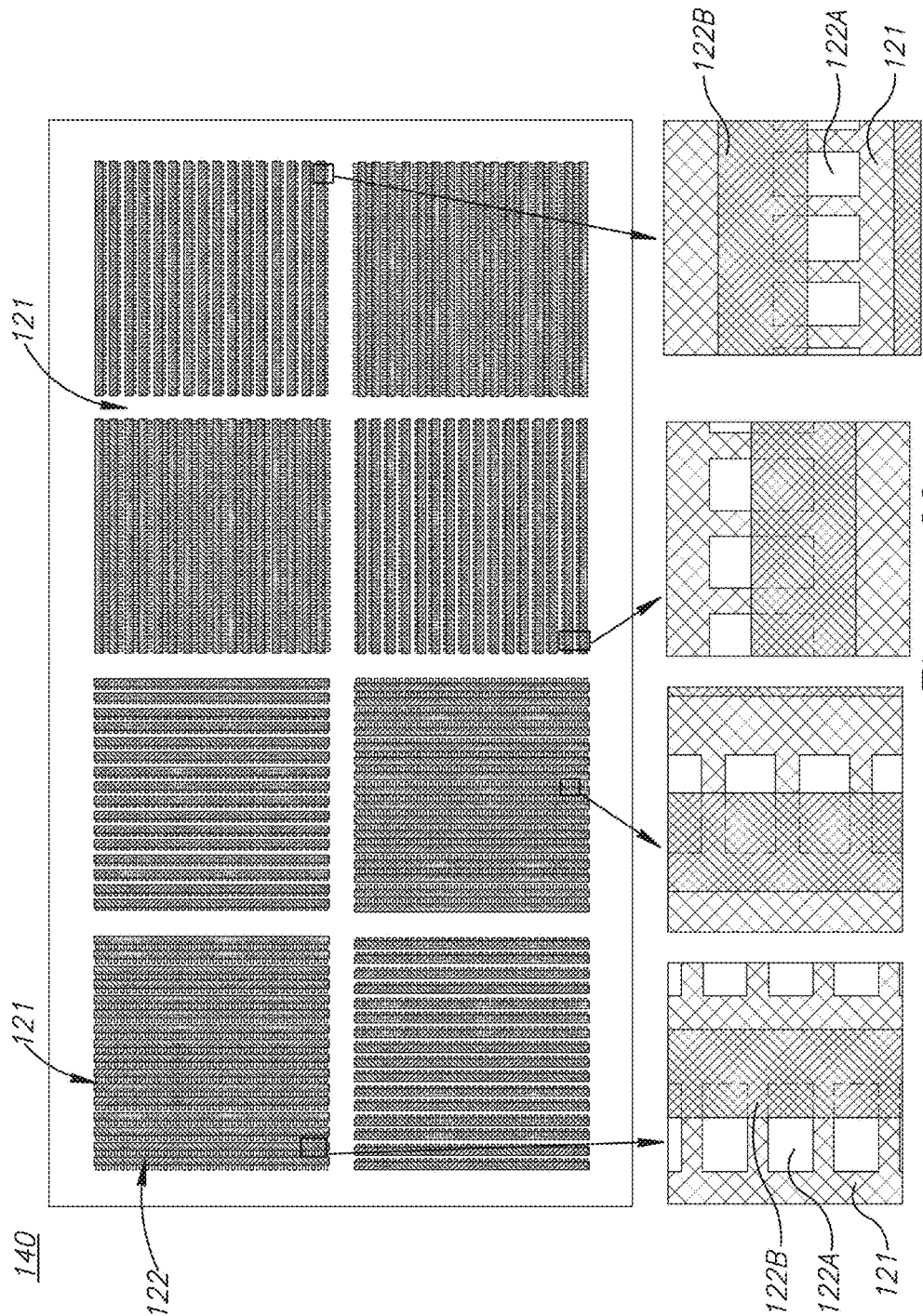
FIG. 23 is a high level schematic illustration of several SCOL target DSA designs, according to some embodiments of the invention.
Figure 24:
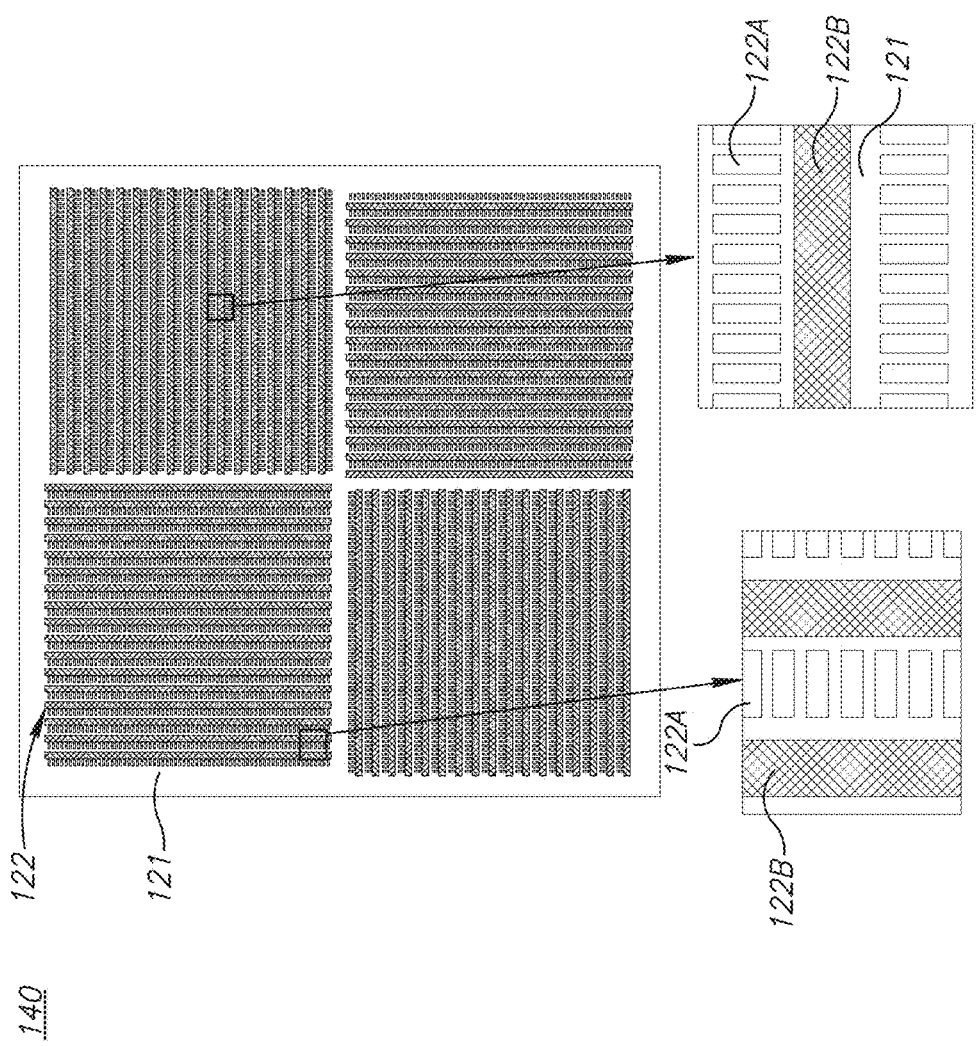
FIG. 24 is a high level schematic illustration of several SCOL target DSA designs, according to some embodiments of the invention.

FIG. 22-24 are high level schematic illustrations of several SCOL target DSA designs, according to some embodiments of the invention. SCOL target structures 122 and backgrounds 121 may be likewise segmented, e.g., using the DSA process, to enhance production and measurement accuracy. Target elements of either or both previous layer 130 and current layer 135, as well as the respective backgrounds, may be segmented. As a non-limiting example, in FIGS. 22-24 various segmentation possibilities are shown for the previous layer's target elements. However, segmentation of current layer target elements and of background sections is also included in the present disclosure.

FIG. 22-24 schematically illustrates segmented previous layer target elements 122A as being composed of segmented gaps while current layer target elements 122B are unsegmented and overlap to different extents with previous layer target elements 122A (no overlap in FIGS. 22 and 24, partial overlap in FIG. 23). In certain embodiments, any of target structures 122, target elements 122A, 122B and/or background features may be segmented, e.g., in a mutually perpendicularly manner, depending on specific target design requirements. The DSA process may be implemented to any of the target and background elements, and any of which may be respectively segmented.

Method 400 may comprise producing AIM, AIMID, BiB, BLOSSOM or SCOL metrology targets and their equivalents or variants by a directed self-assembly (DSA) process, wherein at least one target element of the target is distinguished from its background by at least one characteristic of the DSA process, such as a direction, a spatial frequency, dimensions and spacing of DSA guiding lines. Any layer of the target may be produced by the DSA process and any relative line orientation may be used. Segmentation characteristics may vary within targets, within target structures and within background regions. A computer program product is provided, comprising a computer readable storage medium having computer readable program embodied therewith. The computer readable program is configured to design metrology targets of various types according to the principles disclosed above, e.g., compatibly with method 400. Also, a computer program product is provided, comprising a computer readable storage medium having computer readable program embodied therewith. The computer readable program is configured to carry out metrology measurements of targets produced according to the principles disclosed above, e.g., according to method 400. See further stages of method 400 in FIG. 27 below. Design and production elements and steps regarding DSA production of target elements may be incorporated to design and production of any of the designs of metrology targets 140 that are illustrated above.

FIG. 25 is a high level flowchart illustrating a method 200, according to some embodiments of the invention. Method 200 may comprise stages for producing, preparing and/or using targets 140, such as any of the following stages, irrespective of their order.

Method 200 may comprise producing a polymer surface by a directed self-assembly (DSA) process (stage 205), selecting rod-like molecules to bind to linearly ordered polymer molecules stronger than to unordered polymer molecules (stage 210), binding rod-like molecules onto a polymer surface which comprises ordered regions and unordered regions (stage 220), configuring a dissociative treatment to remove the rod-like molecules which are bound to the unordered polymer molecules while maintaining the bonds between the rod-like molecules and the linearly ordered polymer molecules (stage 230) and applying a dissociative treatment to the polymer surface (stage 240); yielding the polymer surface with rod-like molecules bound exclusively to the ordered regions (stage 250).

Method 200 may comprise selecting the rod-like molecules from cellulose, nanotubes and rigid-rod polymers (stage 212) e.g., selecting the rod-like molecules to be cellulose molecules having a crystalline form which depends upon a level of order on the bound region (stage 213). Method 200 may further comprise creating topographical differences between the ordered and the unordered regions (stage 215) and/or at least partly etching away the unordered regions (stage 218). Method 200 may further comprise any of the stages: configuring the rod-like molecules to comprise bridging molecule(s) (stage 222), selecting the bridging molecule(s) to define the binding strength onto ordered and unordered regions (stage 224) and selecting the bridging molecule(s) as polymer surface molecule(s) (stage 226).

Method 200 may comprise etching away the unordered regions with the rod-like molecules protecting the ordered regions from the etching (stage 260) and/or using the rod-like molecules as a hard mask for applying additional process steps (stage 270). Thus, method 200 may comprise producing diverse metrology targets using the DSA process and the distinguishing of ordered regions using the rod-like molecules (stage 280), for example segmenting target elements and/or their respective background (stage 282) and/or distinguishing target elements for their respective background by at least one characteristic of the DSA process (stage 285).

Method 200 may further comprise adjusting metrology measurement algorithms to the produced targets (stage 290).

Figure 26:
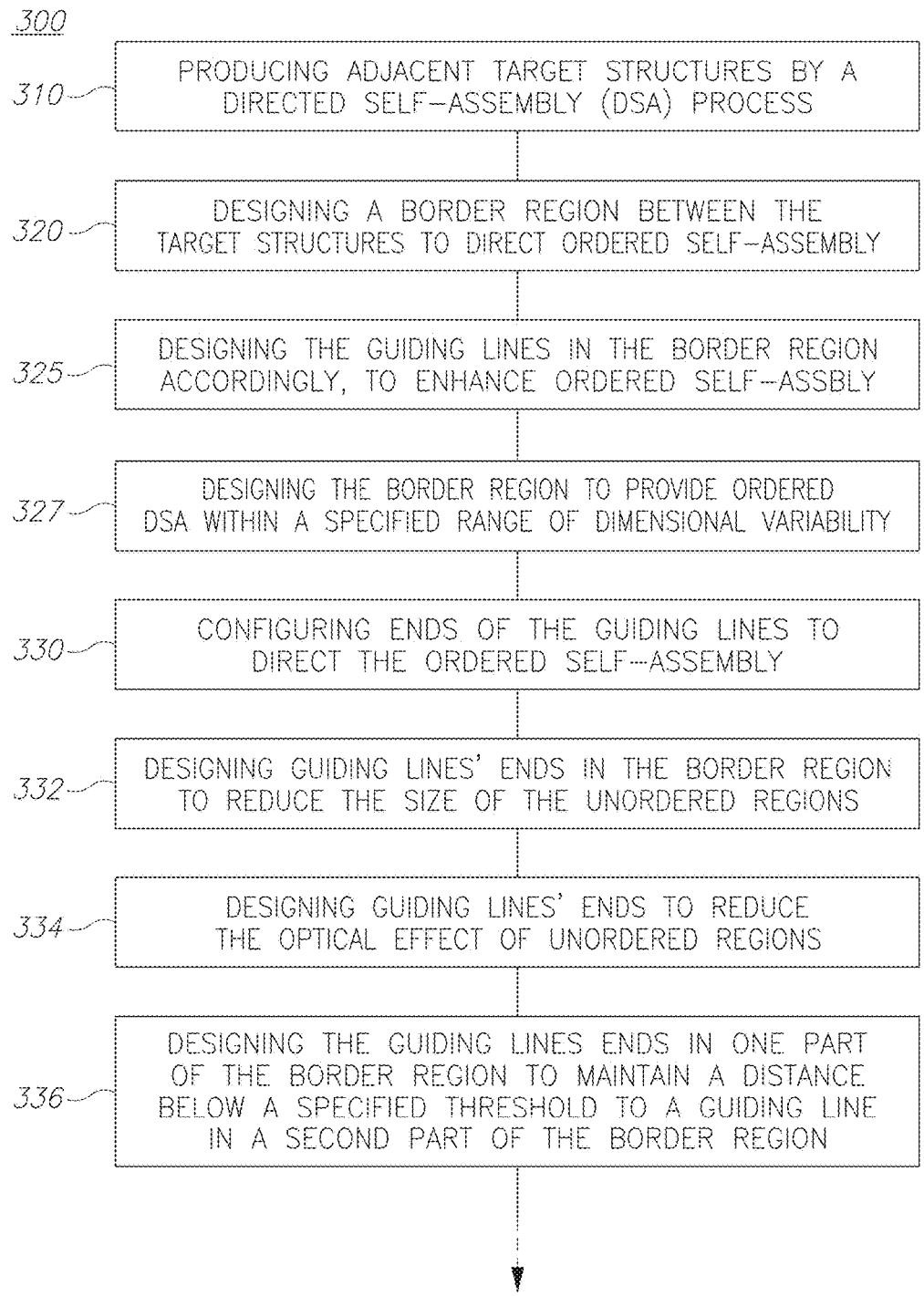
FIG. 26 is a high level flowchart illustrating methods, according to some embodiments of the invention; and, FIG. 27 is a high level flowchart illustrating methods, according to some embodiments of the invention.

FIG. 26 is a high level flowchart illustrating a method 300, according to some embodiments of the invention. Method 300 may comprise stages for producing, preparing and/or using targets 140, such as any of the following stages, irrespective of their order.

Method 300 may comprise producing adjacent target structures by a directed self-assembly (DSA) process (stage 310), designing border regions between the target structures to direct ordered self-assembly (stage 320), e.g., by configuring ends of the guiding lines to direct the ordered self-assembly (stage 330).

Method 300 may further comprise selecting the specified range of dimensional variability of the targets or the specified threshold between adjacent target structures over the border regions to correspond to a specified maximal process inaccuracy associated with a respective guideline production process (stage 340) and designing the border region to yield parallel self-assembly of the polymer molecules in the DSA process (stage 350).

Method 300 may comprise designing guiding lines ends in the border regions to enhance ordered self-assembly (stage 325) and/or designing the border regions to provide ordered DSA within a specified range of dimensional variability (stage 327). Method 300 may comprise designing guiding lines ends in the border region to reduce the size of the unordered regions (stage 332) and/or designing guiding lines ends to reduce the optical effect of unordered regions (stage 334) and/or designing the guiding lines ends in one part of the border region to maintain a distance below a specified threshold to a guiding line in a second part of the border region (stage 336).

Method 300 may comprise selecting the specified threshold to be a maximal border region width defined by the process inaccuracy (stage 345)

Method 300 may comprise producing the guiding line ends to have end-sections which are parallel to adjacent elements (stage 360) and/or designing the guiding lines ends in one part of the border region to be parallel to (an adjacent perpendicular) a guiding line in a second part of the border region (stage 362) and/or producing some of the guiding line ends to protrude beyond other guiding line ends (stage 370).

Method 300 may comprise specifically designing border regions in a metrology target according to these principles and with respect to local considerations (stage 380), producing any of the target designs (stage 385) and adjusting metrology measurement algorithms to the designs of the border regions (stage 390).

FIG. 27 is a high level flowchart illustrating a method 400, according to some embodiments of the invention. Method 400 may comprise stages for producing, preparing and/or using targets 140, such as any of the following stages, irrespective of their order.

Method 400 may comprise designing a metrology target to be produced by a directed self-assembly (DSA) process (stage 410) and/or producing a metrology target using a DSA process (stage 420) comprising distinguishing at least one target element from its background by at least one characteristic of the DSA process (stage 430).

For example, method 400 may comprise distinguishing target elements from their respective background regions by segmenting either or both target elements and the respective background regions (stage 440) and optionally implementing the segmentation using the DSA process (stage 450). Optionally, method 400 may comprise designing at least one target element to be a space in a DSA-produced background (stage 460).

Method 400 may further comprise designing at least one target layer to be produced by DSA (stage 412) and/or designing any of SCOL, AIM, AIMID, BiB and BLOSSOM targets as DSA based targets (stage 415).

Method 400 may further comprise selecting the DSA characteristic as any of the presence, the direction, the spatial frequency and the dimensions of the guidelines (stage 432), for example, distinguishing target elements from their respective background regions through a direction of DSA guiding lines (stage 435).

Method 400 further comprises adjusting metrology measurement algorithms to the designed targets (stage 470).

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A metrology target comprising:
   a polymer material, wherein a surface of the polymer material comprises ordered regions including linearly arranged polymer molecules and unordered regions including unordered polymer molecules; and
   elongated molecules bound to the ordered regions of the polymer surface, wherein a binding strength between the elongated molecules and the ordered regions is greater than a binding strength between the elongated molecules and the unordered polymer molecules.

2. The metrology target of claim 1, wherein at least one of the elongated molecules and the polymer surface are configured to enable distinction between the elongated molecules and the unordered regions using polarized light.

3. The metrology target of claim 1, wherein the unordered regions are at least partly etched away, wherein the elongated molecules protect the ordered regions from etching.

4. The metrology target of claim 1, wherein the polymer surface is produced by a DSA process.

5. The metrology target of claim 1, wherein the ordered regions and the unordered regions are topographically different.

6. The metrology target of claim 1, wherein the elongated molecules comprise at least one of cellulose molecules, nanotubes or rigid-rod polymers.

7. The metrology target of claim 1, wherein the elongated molecules comprise cellulose molecules including a crystalline structure dependent upon a level of order in the ordered region.

8. The metrology target of claim 1, wherein the elongated molecules comprise at least one bridging molecule selected to define the binding strength between the elongated molecules and the ordered regions and the binding strength between the elongated molecules and the unordered polymer molecules.

9. The metrology target of claim 1, wherein the at least one bridging molecule comprises at least one of the polymer molecules of the polymer surface.

10. A hard mask comprising:
    elongated molecules bound onto a portion of a surface of a polymer material, wherein the surface comprises:
    ordered regions including linearly arranged polymer molecules; and
    unordered regions including unordered polymer molecules, wherein a binding strength between the elongated molecules and the ordered regions is greater than a binding strength between the elongated molecules and the unordered polymer molecules.

11. The hard mask of claim 10, wherein the polymer surface is produced by a DSA process.

12. The hard mask of claim 10, wherein the elongated molecules comprise at least one of cellulose molecules, nanotubes or rigid-rod polymers.

13. The hard mask of claim 10, wherein the elongated molecules comprise cellulose molecules including a crystalline structure dependent upon a level of order in the ordered region.

14. The hard mask of claim 10, wherein the elongated molecules comprise at least one bridging molecule selected to define the binding strength between the elongated molecules and the ordered regions and the binding strength between the elongated molecules and the unordered polymer molecules.

15. The hard mask of claim 14, wherein the at least one bridging molecule comprises at least one of the polymer molecules of the polymer surface.

16. A metrology target comprising:
    at least one layer produced by a directed self-assembly (DSA) process, the at least one layer comprising:
    at least one target element and a background region, wherein at least one characteristic of the DSA process of the at least one target element is different from the background region.

17. The metrology target of claim 16, wherein the at least one characteristic of the DSA process is configured to enable distinction between the at least one target element and the background associated with the at least one target element using polarized light.

18. The metrology target of claim 16, wherein the at least one characteristic of the DSA process is selected from at least one of a presence, a direction, a spatial frequency or dimensions of DSA guiding lines.

19. The metrology target of claim 16, wherein the metrology target comprises: at least one of a SCOL target, an AIM target, an AIMID target, a BLOSSOM target, or a BiB target.

20. The metrology target of claim 16, wherein the at least one layer comprises at least one of a previous layer or a current layer of the metrology target.

21. A metrology target comprising:
    at least two adjacent target structures produced by a directed self-assembly (DSA) process, wherein a border region between the target structures comprises:
    a first guiding line of a first target structure of the at least two adjacent target structures; and
    a plurality of guiding line ends of respective guidelines of an additional target structure of the at least two adjacent target structures, wherein the plurality of guiding line ends of the border region are configured to maintain a distance below a specified threshold to the first guiding line.

22. The metrology target of claim 21, wherein the specified threshold is selected to yield parallel self-assembly of polymer molecules in the DSA process.

23. The metrology target of claim 21, wherein the plurality guiding line ends are configured to have end-sections parallel to the first guiding line.

24. The metrology target of claim 21, wherein some of the plurality of guiding line ends are configured to protrude beyond one or more additional guiding line ends with respect to the first guiding line.

25. A metrology target comprising:
at least one target element disposed on at least one of a segmented background or a segmented target element, wherein the at least one of the segmented background or the segmented target element comprise:
a polymer material, wherein a surface of the polymer material comprises ordered regions including linearly arranged polymer molecules and unordered regions including unordered polymer molecules; and
elongated molecules bound to the ordered regions of the polymer surface, wherein a binding strength between the elongated molecules and the ordered regions is greater than a binding strength between the elongated molecules and the unordered polymer molecules.

26. A metrology target comprising:
at least one target element disposed on at least one of a segmented background or a segmented target element, wherein the at least one of the segmented background or the segmented target element comprises: elongated molecules bound onto a portion of a surface of a polymer material, wherein the polymer material comprises ordered regions including linearly arranged polymer molecules;
and unordered regions including unordered polymer molecules, wherein a binding strength between the elongated molecules and the ordered regions is greater than a binding strength between the elongated molecules and the unordered polymer molecules.

\* \* \* \* \*